US006716179B2

(12) United States Patent
Burbank et al.

(10) Patent No.: US 6,716,179 B2
(45) Date of Patent: Apr. 6, 2004

(54) SENTINEL NODE LOCATION AND BIOPSY

(75) Inventors: Fred H. Burbank, Laguna Niguel, CA (US); Paul Lubock, Laguna Niguel, CA (US)

(73) Assignee: Senorx, Inc., Aliso Viejo, CA (US)

( * ) Notice: Subject to any disclaimer, the term of this patent is extended or adjusted under 35 U.S.C. 154(b) by 0 days.

(21) Appl. No.: 10/061,706

(22) Filed: Jan. 30, 2002

(65) Prior Publication Data

US 2002/0115943 A1 Aug. 22, 2002

Related U.S. Application Data

(60) Division of application No. 09/727,112, filed on Nov. 29, 2000, now Pat. No. 6,638,234, which is a continuation-in-part of application No. 09/146,185, filed on Sep. 1, 1998, now Pat. No. 6,540,693, and a continuation-in-part of application No. 09/159,467, filed on Sep. 23, 1998, now Pat. No. 6,261,241, and a continuation-in-part of application No. 09/356,187, filed on Jul. 16, 1999, now Pat. No. 6,312,429, and a continuation-in-part of application No. 09/477,255, filed on Jan. 4, 2000, now Pat. No. 6,471,700, and a continuation-in-part of application No. 09/057,303, filed on Apr. 8, 1998, now Pat. No. 6,331,166.
(60) Provisional application No. 60/076,973, filed on Mar. 3, 1998.

(51) Int. Cl.[7] ............................ A61B 10/00; A61B 6/00; A61B 18/18
(52) U.S. Cl. ..................... 600/564; 600/562; 600/431; 606/41; 606/45
(58) Field of Search ............................... 600/564, 562, 600/566–568, 204, 431, 436; 606/167, 170, 185, 186, 45, 46, 41, 47–50; 250/362, 363.02; 607/100, 101, 105, 106, 113, 122

(56) References Cited

U.S. PATENT DOCUMENTS

| 2,032,860 A | 3/1936 | Wappler et al. |
| 2,192,270 A | 3/1940 | McGowan |

(List continued on next page.)

FOREIGN PATENT DOCUMENTS

| DE | 19528440 A1 | 8/1995 |
| EP | 146699 | 9/1984 |

(List continued on next page.)

OTHER PUBLICATIONS

Laura Liberman, MD, et al., *Sentinel Lymph Node Biopsy after Percutaneous Diagnosis of Nonpalpable Breast Cancer*, Radiology, vol. 211. Jun. 1999, pp. 835–844.

(List continued on next page.)

*Primary Examiner*—Charles Marmor
(74) *Attorney, Agent, or Firm*—Edward J. Lynch; Duane Morris LLP

(57) ABSTRACT

A device and system for accessing and anchoring a patient's sentinel lymph node after a radiopharmaceutical is injected at or near a lesion site within a patient's body. The migration of and accumulation of the radiopharmaceutical in a sentinel node of the patient is monitored from outside the patient's body. The sentinel node can then be accessed through a cannula and an anchoring device may be employed to fix the location of the sentinel node. The anchoring device has at least one radially extending members which penetrate into the sentinel node. Preferably, the radially extending members are RF powered to facilitate entry into the sentinel node. With the anchor device secured to the sentinel node as a locator, subsequent procedures may be performed.

10 Claims, 14 Drawing Sheets

U.S. PATENT DOCUMENTS

| | | |
|---|---|---|
| 3,341,417 A | 9/1967 | Sinaiko |
| 3,805,791 A | 4/1974 | Seuberth et al. |
| 3,818,894 A | 6/1974 | Wichterle et al. |
| 3,823,212 A | 7/1974 | Chvapil |
| 3,955,578 A | 5/1976 | Chamness et al. |
| 4,007,732 A | 2/1977 | Kvavle et al. |
| 4,172,449 A | 10/1979 | LeRoy et al. |
| 4,197,846 A | 4/1980 | Bucalo |
| 4,202,338 A | 5/1980 | Bitrolf |
| 4,243,048 A | 1/1981 | Griffin |
| 4,276,885 A | 7/1981 | Tickner et al. |
| 4,294,241 A | 10/1981 | Miyata |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,425,908 A | 1/1984 | Simon |
| 4,503,855 A | 3/1985 | Maslanka |
| 4,545,367 A | 10/1985 | Tucci |
| 4,565,200 A | 1/1986 | Cosman |
| 4,576,162 A | 3/1986 | McCorkle |
| 4,592,356 A | 6/1986 | Gutierrez |
| 4,616,656 A | 10/1986 | Nicholson et al. |
| 4,638,802 A | 1/1987 | Okada |
| 4,643,187 A | 2/1987 | Okada |
| 4,647,480 A | 3/1987 | Ahmed |
| 4,682,606 A | 7/1987 | DeCaprio |
| 4,693,237 A | 9/1987 | Hoffman et al. |
| 4,718,419 A | 1/1988 | Okada |
| 4,724,836 A | 2/1988 | Okada |
| 4,774,948 A | 10/1988 | Markham |
| 4,813,062 A | 3/1989 | Gilpatrick |
| 4,847,049 A | 7/1989 | Yamamoto |
| 4,863,470 A | 9/1989 | Carter |
| 4,909,250 A | 3/1990 | Smith |
| 4,959,547 A | 9/1990 | Carroll et al. |
| 4,966,583 A | 10/1990 | Debbas |
| 5,007,908 A | 4/1991 | Rydell |
| 5,024,617 A | 6/1991 | Karpiel |
| 5,035,696 A | 7/1991 | Rydell |
| 5,047,027 A | 9/1991 | Rydell |
| 5,059,197 A | 10/1991 | Urie et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| RE33,925 E | 5/1992 | Bales et al. |
| 5,111,828 A | 5/1992 | Kornberg et al. |
| 5,133,359 A | 7/1992 | Kedem |
| RE34,056 E | 9/1992 | Lindgren et al. |
| 5,147,307 A | 9/1992 | Gluck |
| 5,151,598 A | 9/1992 | Denen |
| 5,158,084 A | 10/1992 | Ghiatas |
| 5,158,561 A | 10/1992 | Rydell et al. |
| 5,163,938 A | 11/1992 | Kambara et al. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,217,458 A | 6/1993 | Parins |
| 5,221,269 A | 6/1993 | Miller et al. |
| 5,224,488 A | 7/1993 | Neuffer |
| 5,234,426 A | 8/1993 | Rank et al. |
| 5,236,410 A | 8/1993 | Granov et al. |
| 5,281,218 A | 1/1994 | Imran |
| 5,281,408 A | 1/1994 | Unger |
| 5,282,781 A | 2/1994 | Liprie |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,334,381 A | 8/1994 | Unger |
| 5,335,671 A | 8/1994 | Clement |
| 5,344,420 A | 9/1994 | Hilal et al. |
| 5,353,804 A | 10/1994 | Kornberg et al. |
| 5,368,030 A | 11/1994 | Zinreich et al. |
| 5,376,094 A | 12/1994 | Kline |
| 5,380,321 A | 1/1995 | Yoon |
| 5,395,312 A | 3/1995 | Desai |
| 5,395,319 A | 3/1995 | Hirsh et al. |
| 5,409,004 A | 4/1995 | Sloan |
| 5,415,656 A | 5/1995 | Tihon et al. |
| 5,417,687 A | 5/1995 | Nardella et al. |
| 5,417,697 A | 5/1995 | Wilk et al. |
| 5,422,730 A | 6/1995 | Barlow et al. |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,503 A | 8/1995 | Considine et al. |
| 5,449,382 A | 9/1995 | Dayton |
| 5,462,553 A | 10/1995 | Dolgin |
| 5,470,308 A | 11/1995 | Edwards et al. |
| 5,484,436 A | 1/1996 | Eggers et al. |
| 5,487,385 A | 1/1996 | Avitall |
| 5,488,958 A | 2/1996 | Topel et al. |
| 5,494,030 A | 2/1996 | Swartz et al. |
| 5,501,654 A | 3/1996 | Failla et al. |
| 5,526,822 A | 6/1996 | Burbank et al. |
| 5,542,948 A | 8/1996 | Weavers et al. |
| 5,549,560 A | 8/1996 | Van de Wijdeven |
| 5,607,389 A | 3/1997 | Edwards et al. |
| 5,611,803 A | 3/1997 | Heaven et al. |
| 5,636,255 A | 6/1997 | Ellis |
| 5,643,246 A | 7/1997 | Leeb et al. |
| 5,643,282 A | 7/1997 | Kieturakis |
| 5,646,146 A | 7/1997 | Faarup et al. |
| 5,649,547 A | 7/1997 | Ritchart et al. |
| 5,653,718 A | 8/1997 | Yoon |
| 5,665,085 A | 9/1997 | Nardella |
| 5,674,184 A | 10/1997 | Hassler, Jr. |
| 5,676,925 A | 10/1997 | Klaveness et al. |
| 5,683,384 A | 11/1997 | Gough et al. |
| 5,687,739 A | 11/1997 | McPherson et al. |
| 5,688,490 A | 11/1997 | Tournier et al. |
| 5,700,273 A | 12/1997 | Buelna et al. |
| 5,715,825 A | 2/1998 | Crowley |
| 5,720,763 A | 2/1998 | Tovey |
| 5,732,704 A | 3/1998 | Thurston et al. |
| 5,735,847 A | 4/1998 | Gough et al. |
| 5,741,225 A | 4/1998 | Lax et al. |
| 5,749,887 A | 5/1998 | Heske et al. |
| 5,752,972 A | 5/1998 | Hoogeboom |
| 5,755,697 A | 5/1998 | Jones et al. |
| 5,766,163 A | 6/1998 | Mueller et al. |
| 5,769,086 A | 6/1998 | Ritchart et al. |
| 5,772,660 A | 6/1998 | Young et al. |
| 5,775,333 A | 7/1998 | Burbank et al. |
| 5,782,764 A | 7/1998 | Werne |
| 5,782,775 A | 7/1998 | Milliman et al. |
| 5,794,626 A | 8/1998 | Kieturakis |
| 5,795,308 A | 8/1998 | Russin |
| 5,797,907 A | 8/1998 | Clement |
| 5,800,378 A | 9/1998 | Edwards et al. |
| 5,800,445 A | 9/1998 | Ratcliff et al. |
| 5,810,806 A | 9/1998 | Ritchart et al. |
| 5,846,513 A | 12/1998 | Carroll et al. |
| 5,853,366 A | 12/1998 | Dowlatshahi |
| 5,857,463 A | 1/1999 | Thurston et al. |
| 5,868,740 A | 2/1999 | LeVeen et al. |
| 5,876,340 A | 3/1999 | Tu et al. |

| | | | |
|---|---|---|---|
| 5,902,272 A | 5/1999 | Eggers et al. | |
| 5,902,310 A | 5/1999 | Foerster et al. | |
| 5,913,857 A | 6/1999 | Ritchart et al. | |
| 5,916,167 A | 6/1999 | Kramer et al. | |
| 5,925,044 A | 7/1999 | Hofmann et al. | |
| 5,928,150 A | 7/1999 | Call | |
| 5,928,164 A | 7/1999 | Burbank et al. | |
| 5,947,964 A | 9/1999 | Eggers et al. | |
| 5,954,670 A | 9/1999 | Baker | |
| 5,961,458 A | 10/1999 | Carroll | |
| 5,964,716 A | 10/1999 | Gregoire et al. | |
| 5,972,002 A | 10/1999 | Bark et al. | |
| 5,984,919 A | 11/1999 | Hilal et al. | |
| 6,004,269 A | 12/1999 | Crowley et al. | |
| 6,056,700 A | 5/2000 | Burney et al. | |
| 6,063,082 A | 5/2000 | DeVore et al. | |
| 6,161,034 A | 12/2000 | Burbank et al. | |
| 6,234,177 B1 | 5/2001 | Barsch | |
| 6,363,940 B1 * | 4/2002 | Krag | 128/899 |
| 6,484,050 B1 * | 11/2002 | Carroll et al. | 600/436 |
| 2001/0002250 A1 * | 5/2001 | Burbank et al. | 424/9.5 |
| 2002/0058884 A1 * | 5/2002 | Burbank et al. | 600/564 |

FOREIGN PATENT DOCUMENTS

| | | |
|---|---|---|
| EP | 0255123 | 2/1988 |
| EP | 0292936 | 11/1988 |
| EP | 0472368 A2 | 8/1991 |
| EP | 0481685 A1 | 10/1991 |
| EP | 0 472 368 A2 | 2/1992 |
| EP | 0 601 709 A2 | 6/1994 |
| EP | 0667126 A1 | 8/1995 |
| EP | 0 769 281 A2 | 4/1997 |
| EP | 0 797 957 A1 | 10/1997 |
| GB | 2311468 A | 2/1997 |
| WO | 93/14712 | 5/1993 |
| WO | 93/13718 | 7/1993 |
| WO | PCT/GB94/01536 | 7/1994 |
| WO | PCT/GB94/01537 | 7/1994 |
| WO | 94/27670 | 12/1994 |
| WO | WO 95/02370 | 1/1995 |
| WO | 95/02371 | 1/1995 |
| WO | 95/03843 | 2/1995 |
| WO | 96/08208 A1 | 3/1996 |
| WO | WO 97 29702 | 8/1997 |
| WO | 97/29702 A1 | 8/1997 |
| WO | 98/06346 | 2/1998 |
| WO | 98/08441 | 3/1998 |
| WO | 98/24372 | 6/1998 |
| WO | 99/30764 | 6/1999 |
| WO | 99/44506 | 9/1999 |
| WO | WO 00 12009 | 3/2000 |
| WO | 00/16697 | 3/2000 |
| WO | WO 01 49184 | 7/2001 |

OTHER PUBLICATIONS

Mark S. Pack, M.D. Robert S. Thomas, M.D., "Axillary Lymph Node's Dissection: Does It Have a Role In Primary Breast Cancer?", The American Surgeon, Feb. 1996, vol. 62, pp. 159–161.

J. S. Armstrong et al. "Differential marking of excision planes in screened breast lesions by organically coloured gelantins [see comments]" Journal of Clinical Pathology ( Jul. 1990) 43(7):604–7, XP000971447 abstract; tables 1 and 2.

Blackwell Science Ltd., "The Loop Electrode: New Device for US–Guided Interstitial Tissue Ablation Using Radio Frequency Electrosurgery–An Animal Study" Min Incas Ther & Allied Technol 5: 511–516.

F. Burbank, M.D., "Sterotactic Breast Biopsy: Its History, Its Present, and Its Future", The American Surgeon, Feb. 1996, vol. 62, pp. 128–150.

V. Fucci et al. "Large Bowel Transit Times Using Radiopaque Markers in Normal Cats", J. of Am. Animal Hospital Assn., Nov.–Dec. 1995 31 (6) 473–7.

Timothy J. Micklos, "Percutaneous Biopsy Techniques", Manual of Oncologic Therapeutics, (1989/1990), pp. 39–42.

N. E. Schindlbeck et al., "Measurement of Colon Transit Time", J. of Gastroenterology, No. 28, pp. 399–404, 1990.

Whitman et al., "Coaxial Core Needle Biopsy Under Mammographic Guidance: Indications and Applications", AJR:171, Jul. 1998, pp. 67–70.

English Translation of German Application DE 195 28 440 A1, published Aug. 2, 1995.

International Search Report for PCT/US99/21416 mailed May 19, 2000.

International Search Report for PCT/US01/00543, mailed Jul. 19, 2001.

Written Opinion mailed Jul. 18, 2000, PCT Rule 66, for International Application PCT/US/9921416.

* cited by examiner

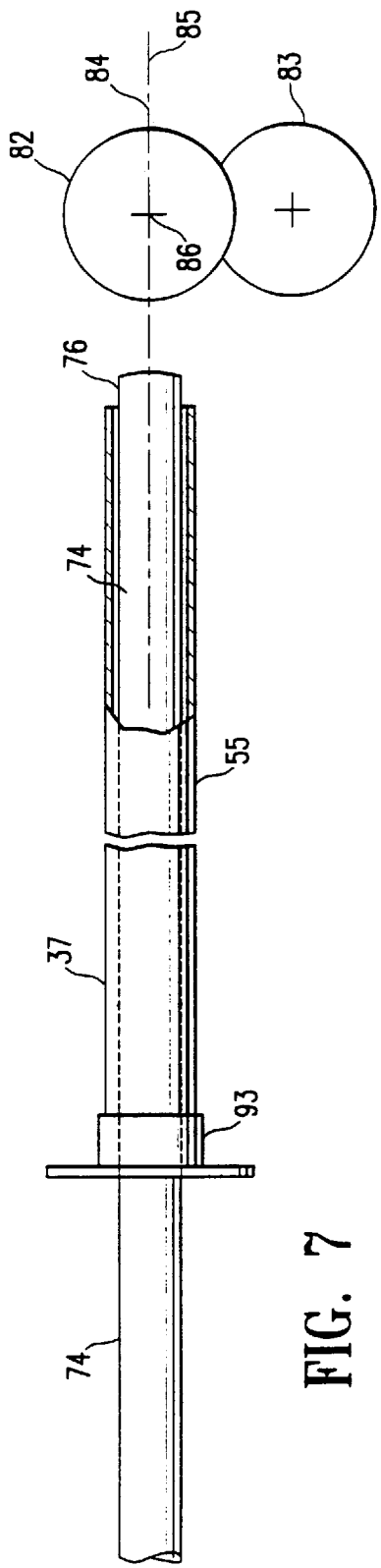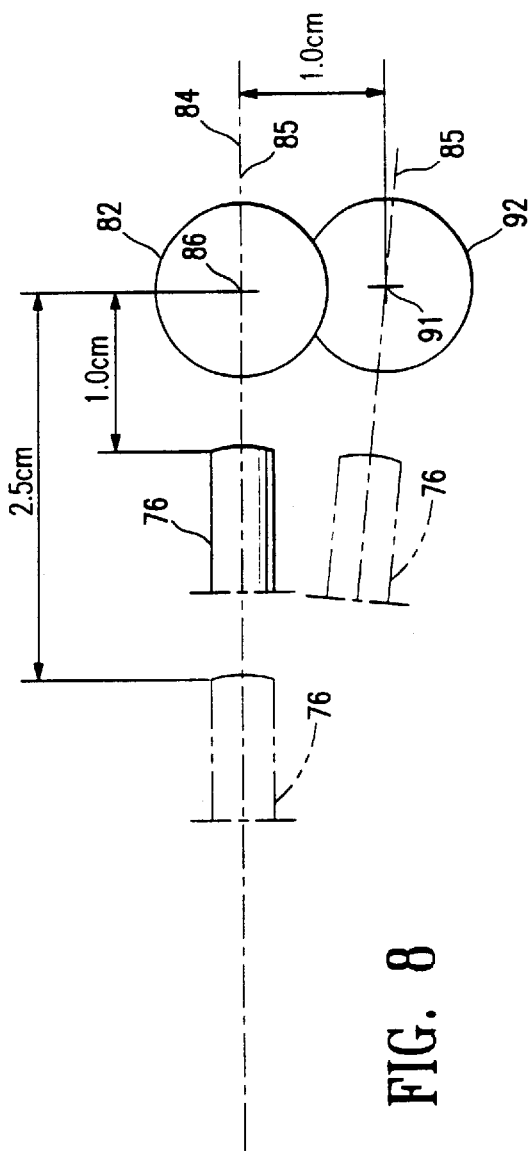
FIG. 7
FIG. 8

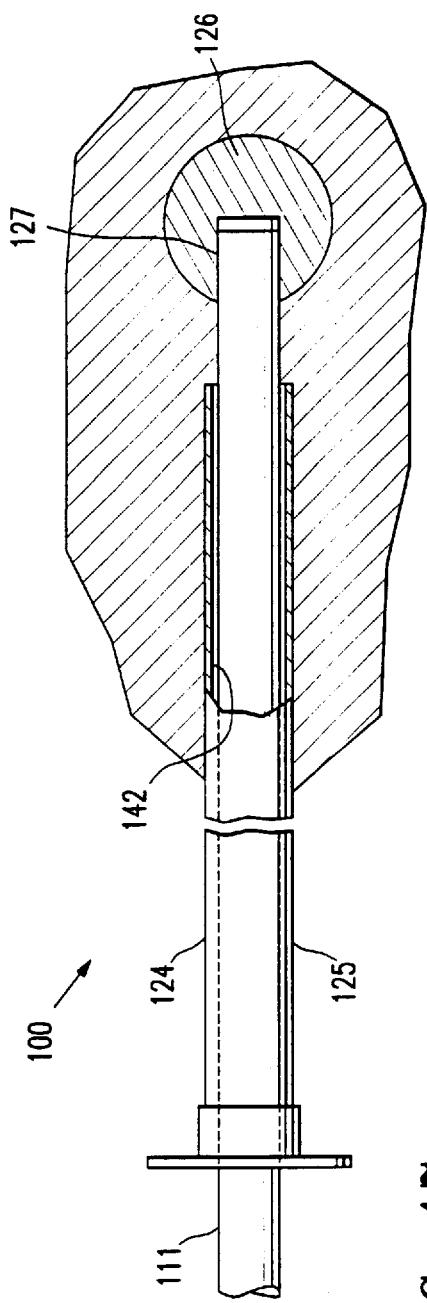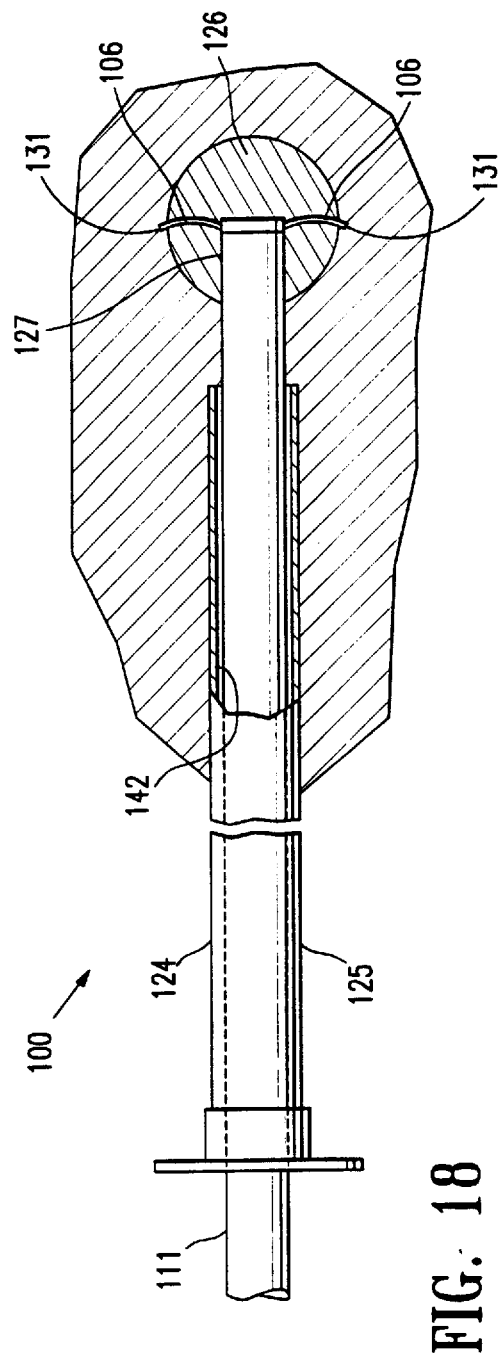

SENTINEL NODE LOCATION AND BIOPSY

RELATED APPLICATIONS

This application is a divisional of copending application Ser. No. 09/727,112, filed Nov. 29, 2000, now U.S. Pat. No. 6,638,234, which is a continuation-in-part of application Ser. No. 09/146,185, filed Sep. 1, 1998, now U.S. Pat. No. 6,540,693; Ser. No. 09/159,467, filed Sep. 23, 1998, now U.S. Pat. No. 6,261,241; Ser. No. 09/356,187, filed Jul. 16, 1999, now U.S. Pat. No. 6,312,429; Ser. No. 09/477,255, filed Jan. 4, 2000, now U.S. Pat. No. 6,471,700; and Ser. No. 09/057,303, filed Apr. 8, 1998, now U.S. Pat. No. 6,331,166, which claims the benefit of provisional patent application Serial No. 60/076,973, filed Mar. 3, 1998, all of which applications and patents are hereby incorporated herein by reference in their entirety and from which priority is hereby claimed under 35 U.S.C. §§119(e) and 120.

BACKGROUND OF THE INVENTION

The invention relates to the field of medical devices and methods used in the treatment of diseases such as cancer which have the ability to metastasize within a patient's body. More specifically, the invention is directed to methods and devices for locating sentinel lymph nodes associated with a lesion site within a patient's body so that the sentinel lymph nodes may thereafter be selectively removed and analyzed to determine whether disease has spread from the primary lesion site to the sentinel lymph nodes. In the case of breast cancer patients, such methods and devices may eliminate the need for complete axillary lymph node dissection in patients who do not require such invasive and debilitating procedures.

With regard to breast cancer patients specifically, the determination of the severity of the disease or staging is frequently determined by the level of lymph node involvement in those lymph nodes which correspond to the primary cancer lesion site in the breast. The lymph nodes which correspond to the breast area are typically located in the armpit or axilla of the patient and are connected to the breast tissue of the patient by a series of lymph ducts. Other likely areas for sentinel nodes include inframammary and submammary locations and elsewhere in the patient's chest. The sentinel lymph nodes can be in fluid communication with other surrounding lymph nodes, however, lymph drainage from the lesion site will first flow to the sentinel lymph nodes. Thereafter, lymph fluid drainage may then continue on to lymph nodes surrounding the sentinel nodes.

Studies have shown that by the time a typical breast cancer lesion reaches the size of 1–2 cm, the cancer will have metastasized to at least one of the sentinel lymph nodes in about one third of patients. Malignant cells break off and drain through the lymph fluid ducts to the lymph nodes and will be apparent in excised lymph nodes if the malignant cells embed in the lymph node. In patients with more advanced disease, the likelihood of spread to sentinel nodes is higher as is the likelihood of spread of the disease to the lymph nodes surrounding the sentinel lymph nodes.

As discussed above, when a tumor lesion is under 1–2 cm, only about ⅓ of patients will have cancer cells in the corresponding lymph nodes, and in the patients where the disease has spread to the lymph nodes, it is often confined to the sentinel lymph nodes.

In the past, a breast cancer patient would normally have a complete axillary lymph node dissection as an adjunct to removal of the primary lesion in the breast. Thus, the patient's entire lymph node system in the armpit area is removed and biopsied to determine the stage of the cancer and what further treatment was required. However, as discussed above, when the lesion is under 1–2 cm, two thirds of the patients had no migration of cancer cells to the lymph nodes at all, and in others, cancer had only migrated to the sentinel lymph nodes. Thus, total axillary lymph node dissection in two-thirds of the cases were unnecessary. It should be noted that total axillary lymph node dissection can be an extremely painful and debilitating procedure for patients who often suffer from severe lymph edema as a result of the body's inability to channel the flow of lymph fluid once most or all of the lymph nodes have been excised.

Thus there is a need for methods and devices that can be used to determine the location of sentinel lymph nodes corresponding to a patient's primary lesion site, and a reliable and noninvasive means of accessing the sentinel lymph nodes to determine whether they are involved in the disease. If the sentinel lymph nodes are determined not to have cancer cells within them, then a total axillary lymph node dissection may be avoided.

It has been known to use radioactive materials or radiopharmaceuticals as localizing agents which can be injected into the area of a primary lesion to monitor the flow of the materials within the patients body using a variety of detectors. Radioactive material such as Technetium 99 m, Indium 111, Iodine 123 or Iodine 125 can be injected in a fluid into the site of a primary lesion and the migration of the radioactive material through lymph ducts to the patient's corresponding sentinel lymph nodes and other surrounding lymph nodes monitored. Although techniques exist to locate the sentinel lymph nodes of a patient with such radiopharmaceutical tagging, what has been needed are methods and devices to precisely locate and access the sentinel lymph nodes of the patient in a noninvasive manner so as to minimize trauma to the patient should it be determined that a total axillary node dissection is unnecessary.

SUMMARY OF THE INVENTION

The invention is directed generally to a method and system for locating and/or accessing specific target sites within the body of a patient. More specifically, the invention is directed to a method and system for locating and accessing a sentinel lymph node of a patient which corresponds to a lesion site within the patient's body.

In one embodiment of the invention, a radioactive material is injected into a patient's body near a primary lesion site or other site of interest within the patient. The approximate position of a sentinel lymph node is within the patient's body is determined by detecting radiation from the radioactive material accumulated within the sentinel lymph node with a radiation detector external to the patient's body. The sentinel lymph node can then be accessed with a cannula having an RF electrode disposed on a distal end of the cannula by activating the RF electrode to ablate tissue while passing the cannula into the patient's body until the distal end of the cannula is disposed adjacent the sentinel lymph node. Thus, access to a patient's sentinel lymph node corresponding to a lesion site is achieved with minimal trauma to the patient, requiring only a hypodermic injection at the lesion site and a channel through the patient's tissue from the outside surface of the skin to the sentinel node, the channel being no larger than the outside dimension of the cannula.

Once the distal end of the cannula is positioned adjacent the sentinel lymph node, an anchor device can be inserted through the cannula and into the sentinel lymph node. The distal end of the anchor device can then be secured to the sentinel lymph node. Once the distal end of the anchor device is secured to the lymph node, the patient can be transferred to a surgical suite and the lymph node surgically removed with the anchor device attached thereto. The anchor device is thus used as a locator for the sentinel lymph node during the surgical procedure.

In some embodiments of a method of the invention, a gamma camera is used to determine the approximate position of the sentinel lymph node within the patient's body prior to accessing the sentinel lymph node with the cannula assembly. Alternatively, a hand held radiation detecting wand or the like can be used to determine the approximate position of the sentinel lymph node within the patient's body. Once the approximate position of a sentinel lymph node is known, the skin of the patient can be marked with a visible mark above the location of the sentinel lymph node prior to accessing the sentinel lymph node with the cannula.

A cannula suitable for use with the method discussed above can have an outer hollow shaft having an inner lumen slidingly disposed about an inner shaft having an RF electrode disposed on the distal end of the inner shaft. The inner shaft can be withdrawn from the outer hollow shaft prior to insertion of the anchor device through the inner lumen of the outer hollow shaft to access a sentinel lymph node. The RF electrode can be an arcuate shaped wire spaced distally from a distal extremity of the distal end of the cannula whereby tissue is ablated along the length of the RF electrode and displaced by the distal end of the cannula as it is advanced through the tissue. Often it is desirable to image the cannula and sentinel lymph node with an ultrasound imaging system during insertion of the cannula into the patient's body.

The proximity of the distal end of the cannula to a radioactive or "hot" sentinel lymph node can be determined by inserting a radiation energy detector probe through the inner lumen of the hollow outer shaft of the cannula and detecting an amount of radiation energy emanating from the tissue along the longitudinal axis of the hollow outer shaft. The hollow outer shaft or the radiation energy detector within the outer hollow shaft can be manipulated while in the patient to detect the amount of radiation energy emanating from various portions of the tissue as they pass in front of the distal end of the radiation energy detector during the manipulation.

The relative amount of radiation detected from the various portions of tissue adjacent the longitudinal axis of the hollow outer shaft can be compared by a visual or audio signal or the like in order for the operator of the system to determine the position of the radiation energy detector where the maximum signal strength exists. The input of the radiation energy detector can be configured so as to maximize output signal strength when a hot sentinel lymph node is disposed directly distal of the distal end of the radiation energy detector. Thus, by maximizing the output signal, the operator can determine the precise location of a hot sentinel lymph node.

Once it is confirmed that the distal end of the outer hollow shaft of the cannula is disposed adjacent a hot sentinel node, the distal end of an anchor device can be inserted through the inner lumen of the outer hollow shaft and secured to the sentinel lymph node. The anchor device can be secured to the sentinel node by deploying at least one extension wire from the distal end of the anchor device into the sentinel lymph node. In addition, an outer extremity of the extension wires can be configured to emit RF energy during deployment of the extension wire so as to ablate tissue adjacent a distal end of the extension wire as it is being advanced through tissue during deployment. Ablation energy activation of the distal ends of the extension wires facilitates penetration of tissue during deployment of the extension wires.

An embodiment of an anchor device for locating a desired portion of tissue within a patient can have an elongate shaft with a proximal and distal end. At least one extension wire is disposed at the distal end of the elongate shaft having a withdrawn configuration and a deployed configuration extending from the distal end of the shaft. The anchor device may also include a deployment actuator disposed proximal of the distal end of the elongate shaft and configured to deploy the extension wire from a retracted configuration to an extended configuration. The deployment actuator of the anchor device can be configured to both extend the extension wires and activate RF energy to the extension wires. One embodiment of an anchor device may have markings spaced at predetermined intervals to delineate the diameter of extension of the extension wires.

In one embodiment of an anchor device, an RF electrode is disposed on the distal end of the elongate shaft configured to ablate and penetrate tissue in a manner similar to the RF electrode on the distal end of the cannula discussed above. An RF electrode on the distal end of the elongate shaft can be in the form of an arcuate wire spaced distally from the distal extremity of the distal end of the elongate shaft and optionally may lie in substantially the same plane as the longitudinal axis of the elongate shaft.

A radiation energy detector for locating the position of radioactive tissue within the body of a patient suitable for use with the methods discussed above can be an elongate shaft having a proximal end, a distal end and an outer transverse dimension of the distal end of up to about 4 mm. A detector body is disposed at the distal end of the elongate shaft which is collimated to receive radiation energy at an angle of up to about 30°, preferably about 10° to about 20° from a longitudinal axis of the elongate shaft. A detector body signal processor is coupled to the detector body. A handle assembly can be disposed at the proximal end of the elongate shaft of the radiation energy detector. The length of the elongate shaft is typically configured to access to a patient's tissue through an inner lumen of a cannula and can be about 5 to about 15 cm.

The detector body signal processor can be configured to emit an audible signal to a user of the detector which has an amplitude which increases logarithmically in relation to an increase in the amount of radiation energy being detected. Alternatively, the detector body signal processor can produce a visual signal to a user of the detector which is proportional in amplitude to the amount of radiation energy being detected.

These and other advantages of the invention will become more apparent from the following detailed description when taken in conjunction with the accompanying exemplary drawings.

BRIEF DESCRIPTION OF THE DRAWINGS

FIG. 7 is an elevational view in partial section of a radiation energy detector disposed within an outer hollow shaft of a cannula with the distal end of the radiation energy detector probe disposed adjacent a first sentinel lymph node and a second sentinel lymph node with the longitudinal axis of the outer hollow shaft and radiation energy detector probe substantially aligned with the center of the first sentinel lymph node.

FIG. 8 is a diagrammatic view of the distal end of a radiation energy detector probe disposed adjacent a first and second sentinel lymph node with the longitudinal axis of the detector probe substantially aligned with the center of the first sentinel lymph node and a phantom outline of the distal end of the radiation energy detector probe wherein the longitudinal axis thereof is substantially aligned with the center of the second sentinel lymph node.

FIG. 17 is an enlarged view in partial longitudinal section of the anchor device of FIG. 16 wherein the distal end of the anchor device is disposed within a sentinel lymph node of the patient with the extension wires in a retracted position.

FIG. 18 is an enlarged view in partial section of the anchor device of FIG. 16 wherein the distal end of the anchor device is disposed within a sentinel lymph node of the patient with the extension wires in an extended position wherein the extension wires have pierced and are mechanically secured to the sentinel lymph node.

DETAILED DESCRIPTION OF THE INVENTION

Figure 1:
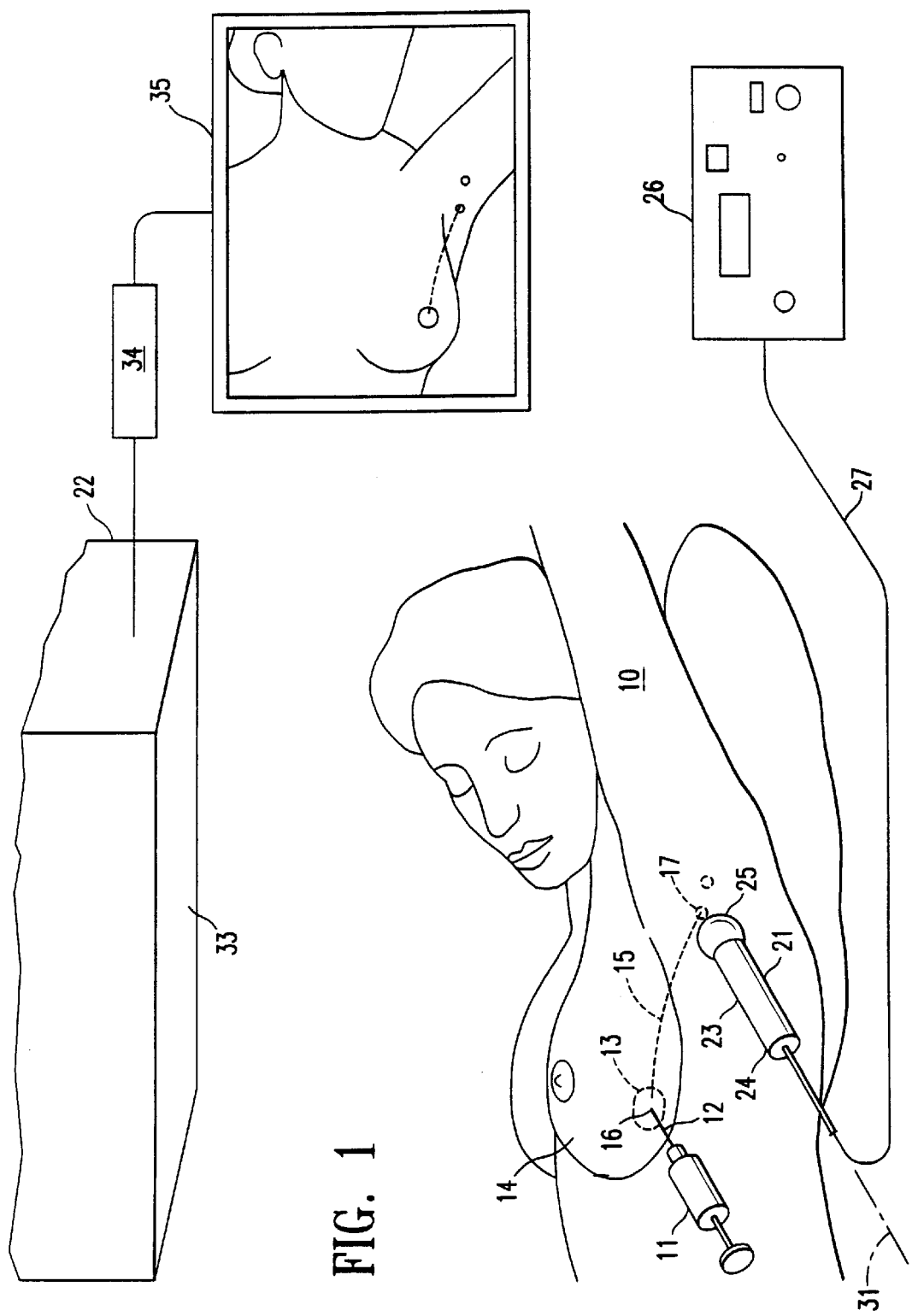
FIG. 1 is a diagrammatic view of a patient being injected with a radioactive material including monitoring of migration of the radioactive material from a lesion site to a sentinel node with a hand held radiation energy detector and a gamma camera.

FIG. 1 illustrates a patient 10 being injected with a radioactive material or radiopharmaceutical via a syringe 11 having a hypodermic needle 12 at a lesion site 13 within the patient's breast 14. Monitoring of migration of the radiopharmaceutical 15 from the injection location 16 in or near the lesion site 13 to a sentinel node 17 is carried out with a hand held radiation energy detector 21 or alternatively a gamma camera 22. The approximate position of the sentinel lymph node 17 is determined by detecting radiation from the radioactive material 15 accumulated within the sentinel lymph node 17 with the hand held radiation detector 21 or the gamma camera 22. Radioactive material 15 such as Technetium 99 m, Indium 111, Iodine 123 or Iodine 125 can be injected in a fluid into the site of a primary lesion 13 and the migration of the radioactive material through lymph ducts to the patient's corresponding sentinel lymph nodes 17 and other surrounding lymph nodes observed.

By correctly timing the observation of the radiation energy signals coming from the patient's body after injection of the radioactive substance 15, it is possible to locate the sentinel lymph nodes 17 corresponding to the lesion site 13. The sentinel lymph nodes 17 corresponding to a given lesion site 13 or other site of interest within a patient's body are those lymph nodes to which lymph fluid emanating from the lesion site drains to first. As discussed above, the lymph nodes which correspond to the breast area are typically located in the armpit of the patient and are connected to the breast tissue 14 of the patient 10 by a series of lymph ducts. Lymph nodes of the axilla are approximately 1 to 2 cm in diameter and are approximately 1 to 5 inches deep in the tissue of the armpit area.

The sentinel lymph nodes 17 can be in fluid communication with other surrounding lymph nodes, however, lymph drainage from the lesion site 13 will first flow to the sentinel lymph nodes 17. Thereafter, lymph fluid drainage may then continue on to lymph nodes surrounding the sentinel nodes 17. Therefore, if a patient 10 is monitored or observed with a hand held radiation detector 21 or gamma camera 22 after the radioactive material 15 has migrated through the lymph ducts to the sentinel lymph nodes 17 but prior to dispersion of the radioactive material to the lymph nodes surrounding the sentinel nodes, an accumulation of radioactive material 15 will be observed in the sentinel lymph nodes 17. These hot sentinel nodes 17 will be clearly distinguishable from surrounding non-radioactive lymph nodes using radiation energy detectors from outside the patient's body 10, thus indicating an approximate position of nodes 17 in a non-invasive manner.

The hand held radiation energy detector 21 has a hand held probe 23 with a proximal end 24 and a distal end 25, a control and display unit 26, and an electrical conduit or cable 27 disposed between the control unit 26 and the hand held probe 23. The control unit 26 can produce an audible or visual output that is commensurate with the amplitude of radiation energy signal being received at the distal end 25 of the hand held probe 23. Typically, the hand held probe 23 will only detect radiation energy which impinges in a proximal direction upon the distal end 25 of the hand held probe 23 at some predetermined angle with respect to a longitudinal axis 31 of the hand held probe 23. Thus, by manipulating the location and direction of the distal end 25 of the hand held probe 23, the approximate location of the hot sentinel lymph nodes 17 within the patient 10 can be determined by maximizing the audio or visual signal generated by the control and display unit 26.

The gamma camera 22 shown in FIG. 1 has a receiver unit 33, a control unit 34 and a display, 35. Radiation energy emitted from the radioactive material 15 injected into the patient 10 travels through the tissue of the patient 10 to the receiver unit 33 which then generates and electrical signal at a location corresponding to the location of the radioactive material source in the patient 10. The signal or hits from the radiation energy which impinges on the receiver 33 can be accumulated or stored such that the display 35 will show all hits received from the various portions of the receiver 33. In this way, the relative location of radioactive material 15 in the patient's body 10 can be seen on the display and particularly locations in the patient's body 10 where radioactive material 15 has accumulated. The skin of the patient 10 can be marked with a visible mark above the location of the sentinel lymph node 17 to indicate the approximate position of the sentinel node 17 for future reference during the procedure.

Figure 2:
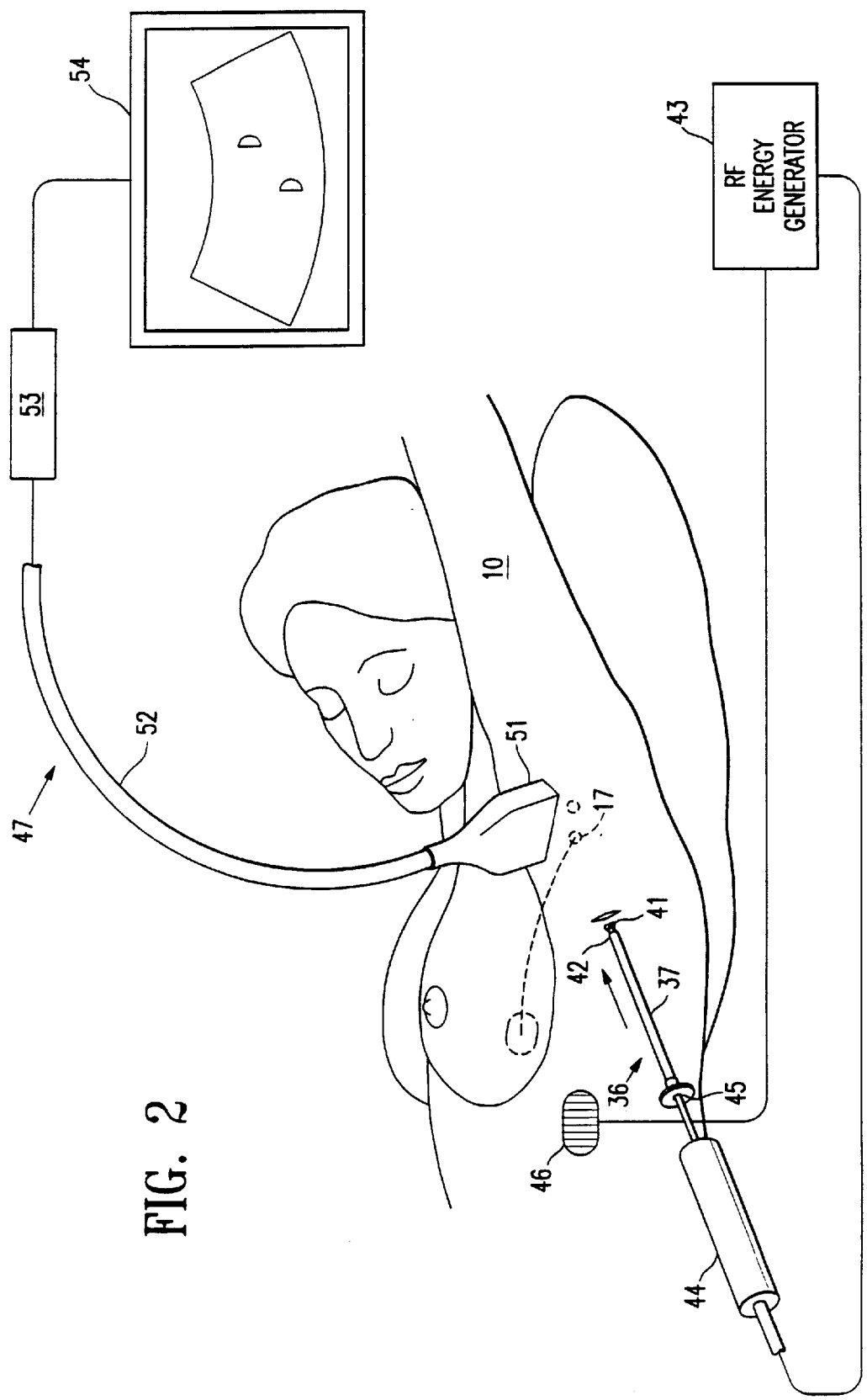
FIG. 2 is a diagrammatic view of a medical procedure having features of the invention including ultrasonic imaging of insertion of a cannula with an RF electrode disposed on the distal end of the cannula.

Once the approximate position of the sentinel lymph nodes 17 of a patient 10 corresponding to a primary lesion site 13 is determined, an access device 36 may be used to breach tissue over the lymph nodes. This allows locating the sentinel nodes 17 with greater precision. FIG. 2 shows ultrasonic imaging of insertion of an access device 36 consisting of a cannula 37 having an RF electrode 41 disposed on the distal end 42 of the cannula 37, an RF energy generator 43 in electrical communication with the RF electrode 41, a cannula handle assembly 44 at a proximal end 45 of the cannula 37 and a ground pad 46 secured to and in electrical communication with the patient's body 10 and the RF generator 43. The sentinel lymph node 17 is accessed by passing the cannula 37 with the RF electrode 41 energized to emit RF energy therefrom into the patient's body 10 until the distal end 42 of the cannula 37 is disposed adjacent the sentinel lymph node 17.

The RF generator 43 for the RF electrode 41 can be any of a variety of standard electrosurgical units generating radiofrequency energy in a range of about 300 to about 6,000 kHz, specifically, about 350 to about 1,000 kHz. Power output for the RF generator 43 can be about 25 to about 150 watts, preferably about 75 to about 125 watts. The RF electrode 41 can be made of a variety of materials, including stainless steel, tungsten, nitinol and the like. The RF electrode material may have a cross section that is round, rectangular, oval or any other suitable configuration and generally has a transverse dimension of about 0.001 to about 0.015 inch, specifically about 0.006 to about 0.010 inch.

Because large arteries and nerves are generally located in the same area as the axillary lymph nodes of a patient 10 and could be compromised without an accurate and noninvasive access device 36, ultrasonic imaging can be used while the cannula 37 is being inserted into the patient 10. An ultrasonic imaging system 47 having a transducer 51, transducer cable 52, control unit 53 and display 54 is shown in FIG. 2. The two sentinel lymph nodes 17 are imaged on the display 54. The relative location of the target sentinel lymph node 17 and cannula 37 can be imaged and monitored during insertion of the cannula 37 to ensure accurate placement of the cannula and avoidance of sensitive anatomical features such as nerves and arteries. Because RF tissue ablation frequently interferes with ultrasonic imaging and the like, it may be desirable to use a system for reduction of such interference such as is taught by copending U.S. patent application Ser. No. 09/527,868, by Dabney et al., filed Mar. 17, 2000, which is hereby incorporated by reference herein in its entirety.

Figure 3:
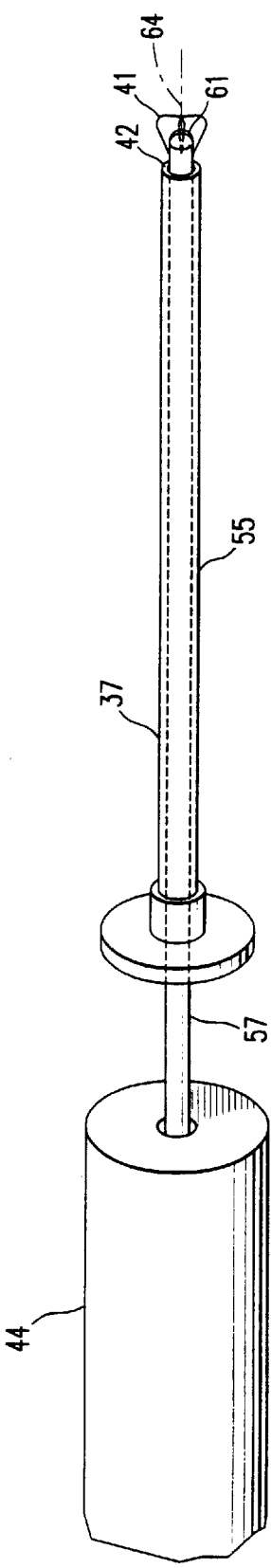
FIG. 3 is a perspective view of a cannula with a two element RF electrode disposed on the distal end of the cannula with the RF electrode in an expanded state.
Figure 5:
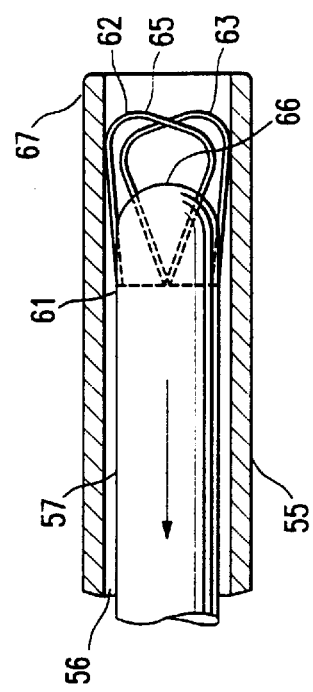
FIG. 5 is an elevational view in partial longitudinal section of the cannula of FIG. 4 with the distal end of the inner shaft retracted into a hollow outer shaft and the RF electrode in a contracted state within the hollow outer shaft.
Figure 4:
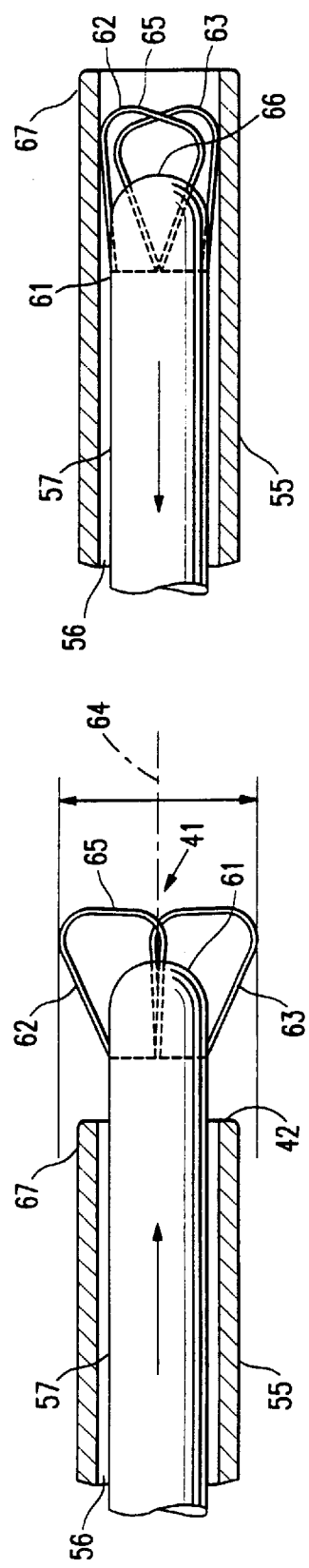
FIG. 4 is an elevational view in partial longitudinal section of a cannula with a two element RF electrode on the distal end in an expanded state.

Referring to FIGS. 3–5 the cannula 37 is shown with a two element RF electrode 41 disposed on the distal end 42 of the cannula 37. A outer hollow shaft 55 having an inner lumen 56 is slidingly disposed about an inner shaft 57 having the RF electrode 41 disposed on the distal end 61 of the inner shaft 57. The RF electrode 41 has a first electrode element 62 and a second electrode element 63 which overlap at the intersection with the longitudinal axis 64 of the cannula 37 extending from the distal end 42. This arrangement allows for the first and second electrode elements 62 and 63 to be expandable to an outer transverse dimension equal to or slightly greater than the circumference of the outer hollow shaft 55. This enables easy insertion of the cannula assembly 37 into the patient 10 as the RF electrode 41 is activated and ablates tissue. The expandability and retractability of the RF electrode 41 allows the inner shaft 57 to be withdrawn from the outer hollow shaft 55 prior to insertion to provide access through the outer hollow shaft 55 to a sentinel lymph node 17 or other tissue area of interest within a patient 10.

The RF electrode 41 is an arcuate shaped wire 65 spaced distally from a distal extremity 66 of the distal end 42 of the cannula 37. When the electrode 41 is activated with RF energy, tissue is ablated along the length of the RF electrode 41 and displaced by the distal end 42 of the cannula 37 as it is advanced through the tissue. FIG. 4 shows the RF electrode 41 on the distal end 42 of the cannula 37 in an expanded state in which the transverse dimension of the RF electrode 41 as a whole is greater than the outer diameter of the outer hollow shaft 55. In FIG. 5, the distal end 61 of the inner shaft 57 of the cannula 37 is withdrawn into the inner lumen 56 of the hollow outer shaft 55 and the RF electrode 41 is in a contracted state within the inner lumen hollow outer shaft.

Figure 6:
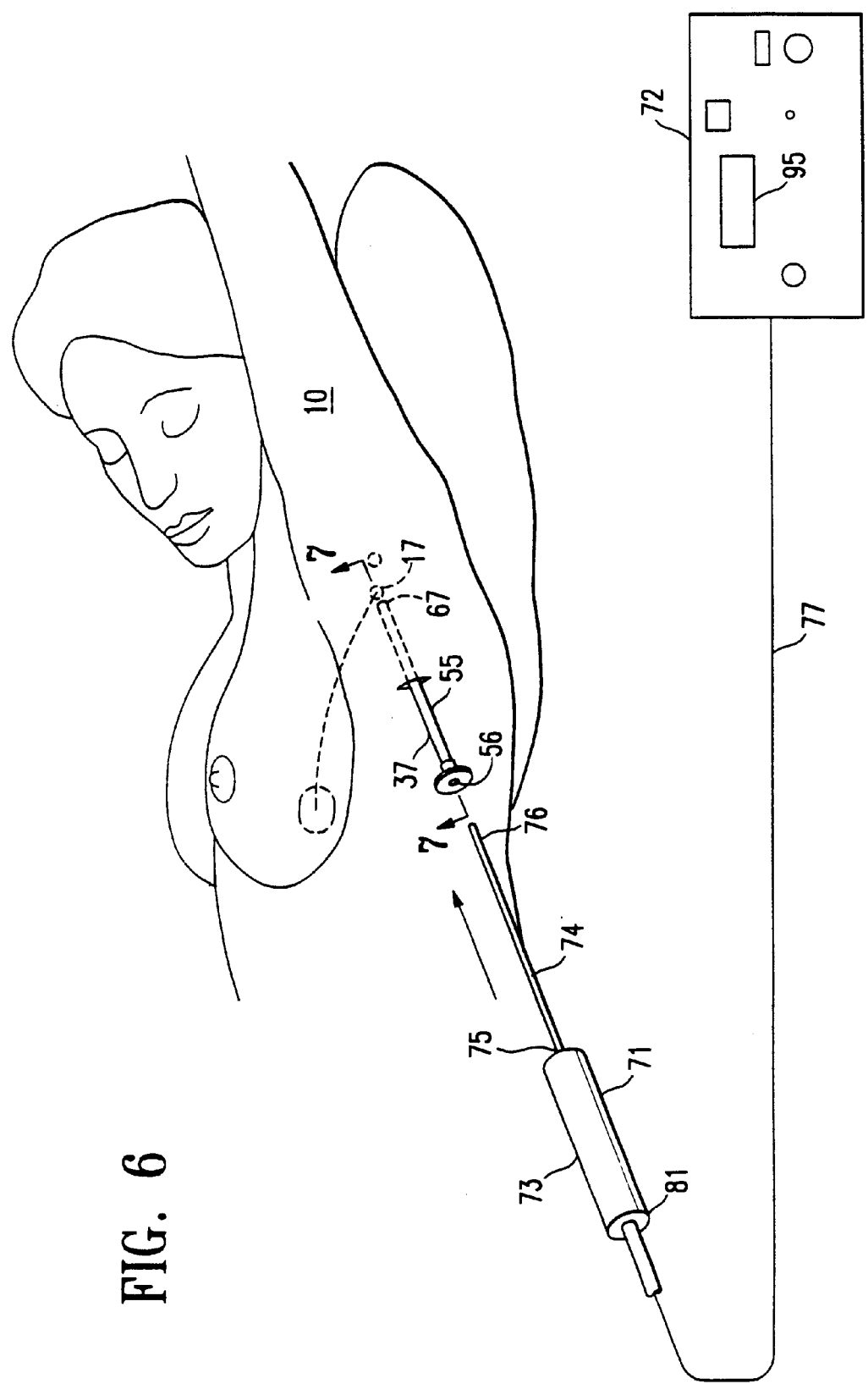
FIG. 6 is a schematic view of an outer hollow shaft of a cannula disposed within a patient with the inner shaft of the cannula withdrawn and the distal end of the outer hollow shaft adjacent a sentinel lymph node. A radiation energy detector probe is positioned for insertion into the outer hollow shaft of the cannula.
Figure 9:
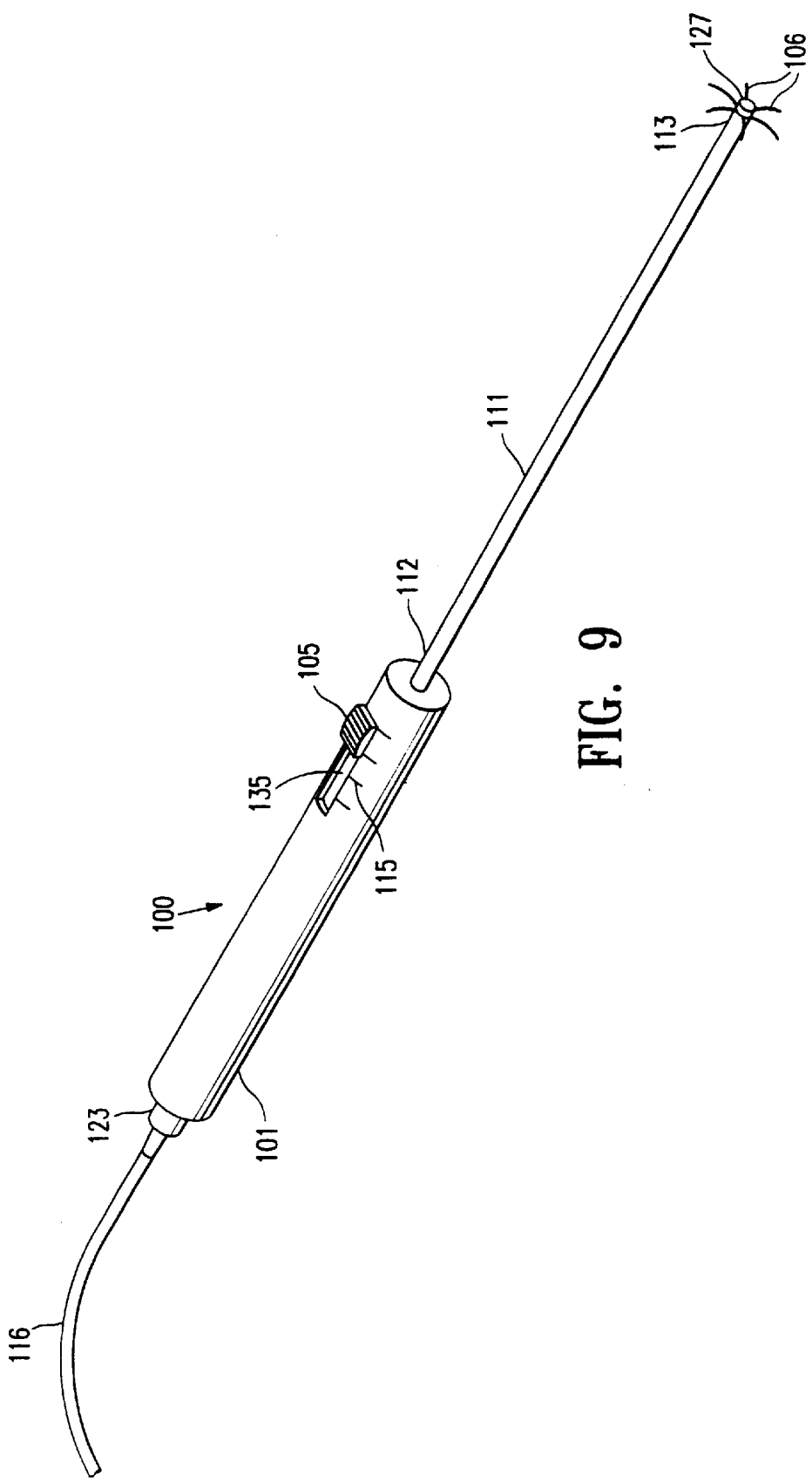
FIG. 9 is a perspective view of an anchor device having features of the invention.

FIG. 6 shows an outer hollow shaft 55 of a cannula 37 disposed within a patient 10 with the inner shaft 57 of the cannula 37 withdrawn and the distal end 67 of the outer hollow shaft 55 adjacent a sentinel lymph node 17. A radiation energy detector 71 having a signal processor unit 72, a handle assembly 73 and a radiation detector probe 74 with a proximal end 75 and distal end 76 is positioned to have the distal end 76 of the radiation energy detector probe 74 inserted into the inner lumen 56 of the outer hollow shaft 55. A cable 77 is in communication with the signal processor unit 72 and a proximal end 81 of the handle assembly 73.

In FIG. 7, the radiation energy detector probe 74 is shown disposed within the outer hollow shaft 55 of the cannula 37. The distal end 76 of the radiation energy detector probe 74 is disposed adjacent a first sentinel lymph node 82 and a second sentinel lymph node 83 with a longitudinal axis 84 of the outer hollow shaft 55 and longitudinal axis 85 of the radiation energy detector probe 74 substantially aligned with the center 86 of the first sentinel lymph node 82. The radiation energy detector probe 74 detects radiation energy emanating from the tissue along the longitudinal axis 85 of the probe 74 in a proximal direction relative to the probe. The hollow outer shaft 55 or the radiation energy detector probe 74 within the outer hollow shaft 55 can be manipulated, as shown in FIG. 8, while in the patient 10 to detect the amount of radiation energy emanating from various portions of the tissue as they pass in front of the distal end 76 of the radiation energy detector probe 74 during the manipulation.

The amount of radiation detected from the various portions of tissue adjacent the longitudinal axis 84 of the hollow outer shaft 55 can be compared by observation of a visual or audio signal or the like generated by the signal processor unit 72 in order for the operator of the system to determine the position of the radiation energy detector probe 74 where the maximum signal strength exists. The input of the radiation energy detector probe 74 at the distal end 76 of the probe 74 can be configured or collimated so as to maximize output signal strength when a sentinel lymph node 17 emitting a relatively large amount of radiation ("hot" sentinel lymph node) is disposed directly distal of the distal end 76 of the radiation energy detector probe 74. Thus, by maximizing the output signal from the signal processor unit 72, the operator can determine the precise location of a hot sentinel lymph node 17 and effectively discriminate surrounding nonradioactive tissue and non-radioactive nodes.

In FIG. 8, the longitudinal axis 85 of the detector probe 74 is substantially aligned with the center 86 of the first sentinel lymph node 82. A phantom outline of the distal end of the radiation energy detector probe is also shown substantially aligned with the center 91 of the second sentinel lymph node 92 after manipulation of the distal end 76 of the radiation energy detector probe 74 from the proximal end 75 of the radiation energy detector probe 74 or the proximal end 93 of the outer hollow shaft 55 of the cannula 37. The diameter of the elongate probe 74 of the radiation energy detector distal end can be about 1 to about 6 mm, specifically about 3 to about 5 mm, and more specifically about 4.0 to about 4.4 mm.

A detector body (not shown) is disposed within the distal end 76 of the elongate radiation energy detector probe 74 which is collimated to receive radiation energy at an angle of up to about 30°, preferably about 10° to about 20°, from a longitudinal axis 85 of the elongate radiation energy detector probe. The detector body can be designed to encompass the radiation emitted from a 1 cm node at a distance of 1 cm. The detector body can be configured or collimated to have enhanced reception of radiation energy from the distal end as opposed to side impingement of radiation energy. The detector body is coupled by the cable 77 to the signal processor unit 72. The detector body can be configured to specifically detect gamma radiation or any other suitable form of radiation energy including alpha or beta radiation. The handle assembly 73 of the radiation energy detector 71 can have a preamplifier within it to increase the signal from the detector body to the signal processor unit 72. The handle 73 typically has a diameter or transverse dimension of about 25–30 mm. The length of the radiation energy detector probe 74 is typically configured to access to a patient's tissue through an inner lumen of a cannula and can be about 5 to about 15 cm.

The signal processor unit 72 of the radiation energy detector 71 can be configured to emit an audible signal to a user of the detector which has an amplitude which increases logarithmically in relation to an increase in the amount of radiation energy being detected. Alternatively, the detector body signal processor unit 72 can produce a visual signal to a user of the detector which is proportional in amplitude to the amount of radiation energy being detected. The signal processor 72 has a display 95 with a digital readout of counts per second and total counts for given time period. The radiation energy detector 71 can typically detect radiation at useable levels from a hot lymph node from a distance of about 10 to about 12 cm, but is most accurate at a distance of about 2 to about 3 cm.

Referring to FIGS. 9–19, an anchor device 100 and use thereof is shown. The anchor device 100 has a housing 101, an inner conductor 102, a main shaft 103 disposed within an inner lumen 104 of the inner conductor 102, an actuator 105 coupled to the inner conductor 102 for extending the extension wires 106 and an RF energy generator 107 switchably coupled to the inner conductor 102 and elongate shaft 111 with a proximal end 112 and distal end 113. At least one extension wire 106 is disposed within the distal end 113 of the elongate shaft 111 coupled to a distal end 114 of the inner conductor 102 and having a withdrawn configuration and a deployed configuration extending radially from the distal end 113 of the shaft 111, or in some other suitable direction. A deployment actuator 105 is disposed proximal of the distal end 113 of the elongate shaft 111 and configured to deploy the extension wire 106 from a retracted configuration to an extended configuration.

Figure 15:
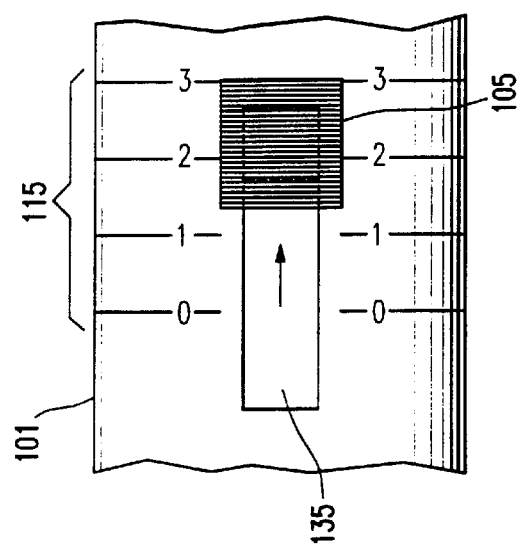
FIG. 15 is a top view of the actuator switch of the anchor device of FIG. 11 in a fully forward distal position corresponding to full extension of the extension wires in an outward radial direction.
Figure 14:
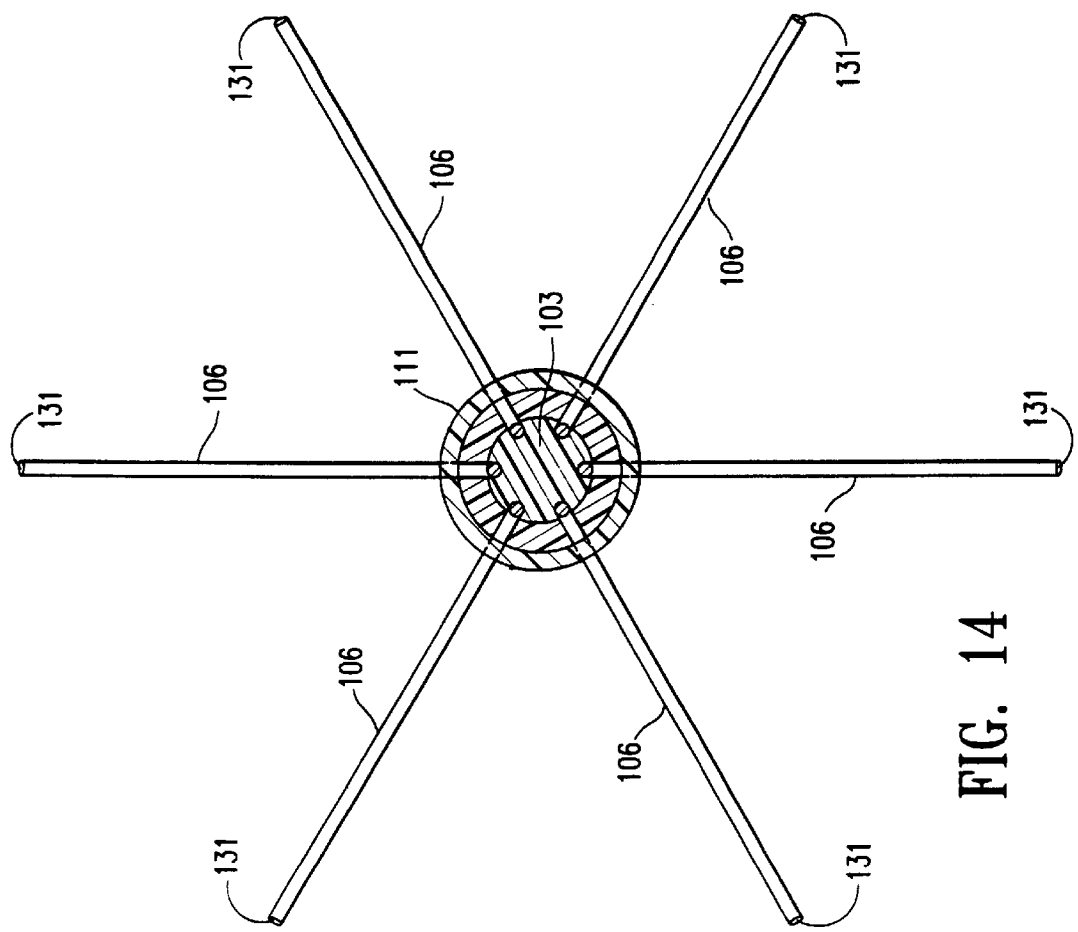
FIG. 14 is an end view in partial transverse cross section of the distal end of the anchor device of FIG. 11 taken along lines 14—14 of FIG. 11.
Figure 16:
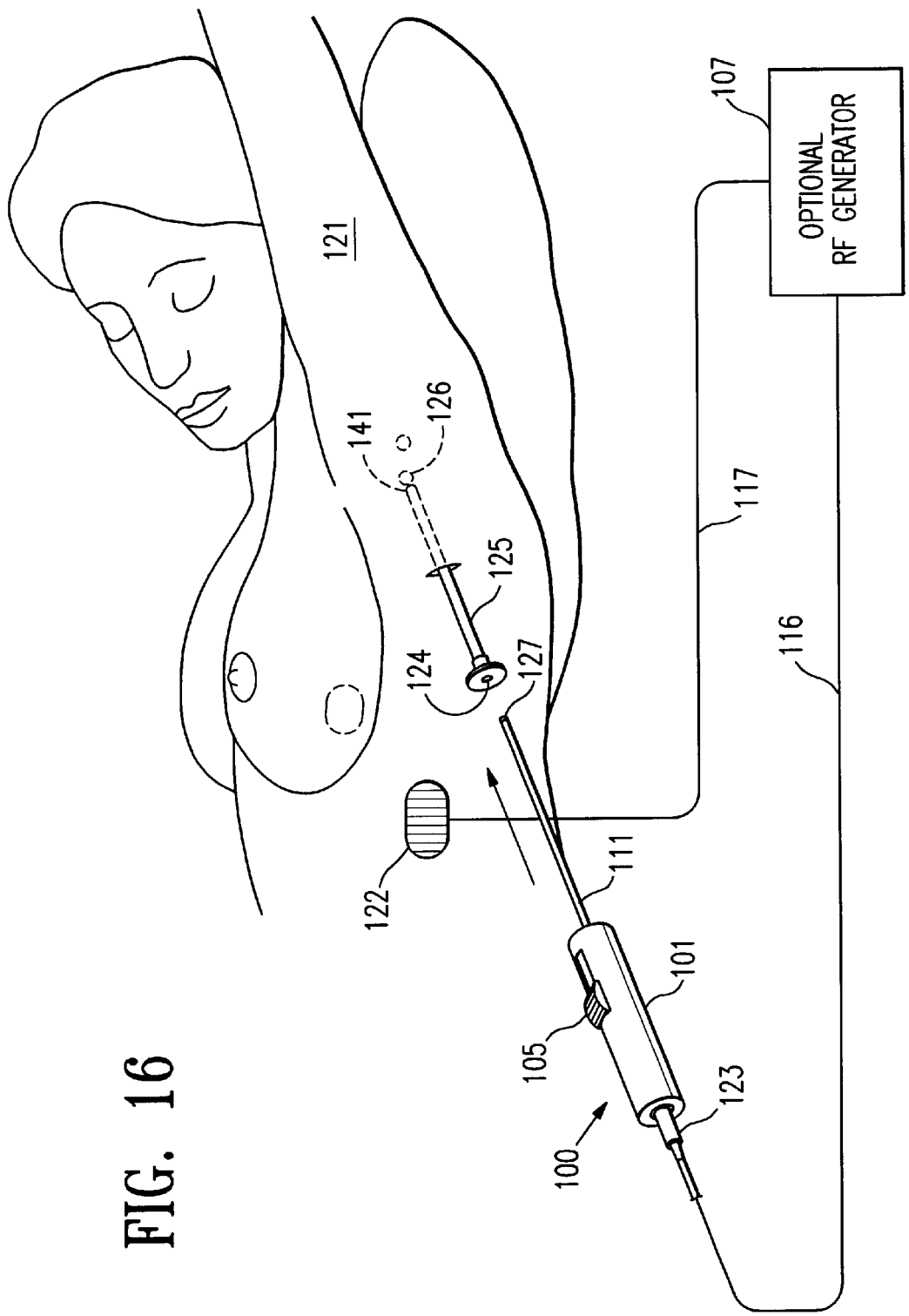
FIG. 16 is a schematic view of an anchor device being inserted into an outer hollow shaft of a cannula the distal end of which is disposed adjacent a sentinel lymph node.

Markings 115 on the housing 101, as shown in FIG. 15, may be spaced at predetermined intervals to delineate the diameter of extension of the at least one extension wire 106 by movement of actuator 105. As shown in FIG. 16, a first electrical conductor 116 can be electrically coupled to the inner conductor 102 and the RF energy generator 107 and a second electrical conductor 117 electrically coupled to the patient 121 as a ground plate 122 for the RF energy generator 107. RF energy may be applied to the extension wires during deployment and extension thereof to aid in the advancement thereof through tissue. However, if RF energy is to be applied, the extension wires should be insulated along their lengths except for the distal tips thereof. The first electrical conductor 116 can be coupled to the extension wires 106 at the proximal end of the shaft 111 with a detachable coupler 123.

The anchor device 100 is generally inserted through the outer hollow shaft 124 of a cannula 125 and into a sentinel lymph node 126. The distal end 127 of the anchor device 100 is then secured to the sentinel lymph node 126. Once the distal end 127 of the anchor device 100 is secured to the lymph node 126, the patient 121 can be transferred to a surgical suite and the lymph node 126 surgically removed with the anchor device 100 attached thereto serving as a locating device.

In the embodiment of the anchor device shown in FIGS. 9–19, the distal end 127 of the anchor device 100 can be secured to the sentinel lymph node 126 by deploying at least one extension wire 106 from the distal end 127 of the anchor device 100 into the sentinel lymph node 126 as shown in FIG. 18. In addition, an outer extremity 131 of the extension wires 106 can be configured to emit RF energy during deployment of the extension wires so as to ablate tissue adjacent the outer extremities 131 of the extension wires 106 to facilitate advancement through tissue during deployment. Radial extension of the extension wires 106 from the anchor device 100 can be from about 1 to about 30 mm, specifically about 3 to about 25 mm, and more specifically about 5 to about 12 mm when deployed fully.

Figure 10:
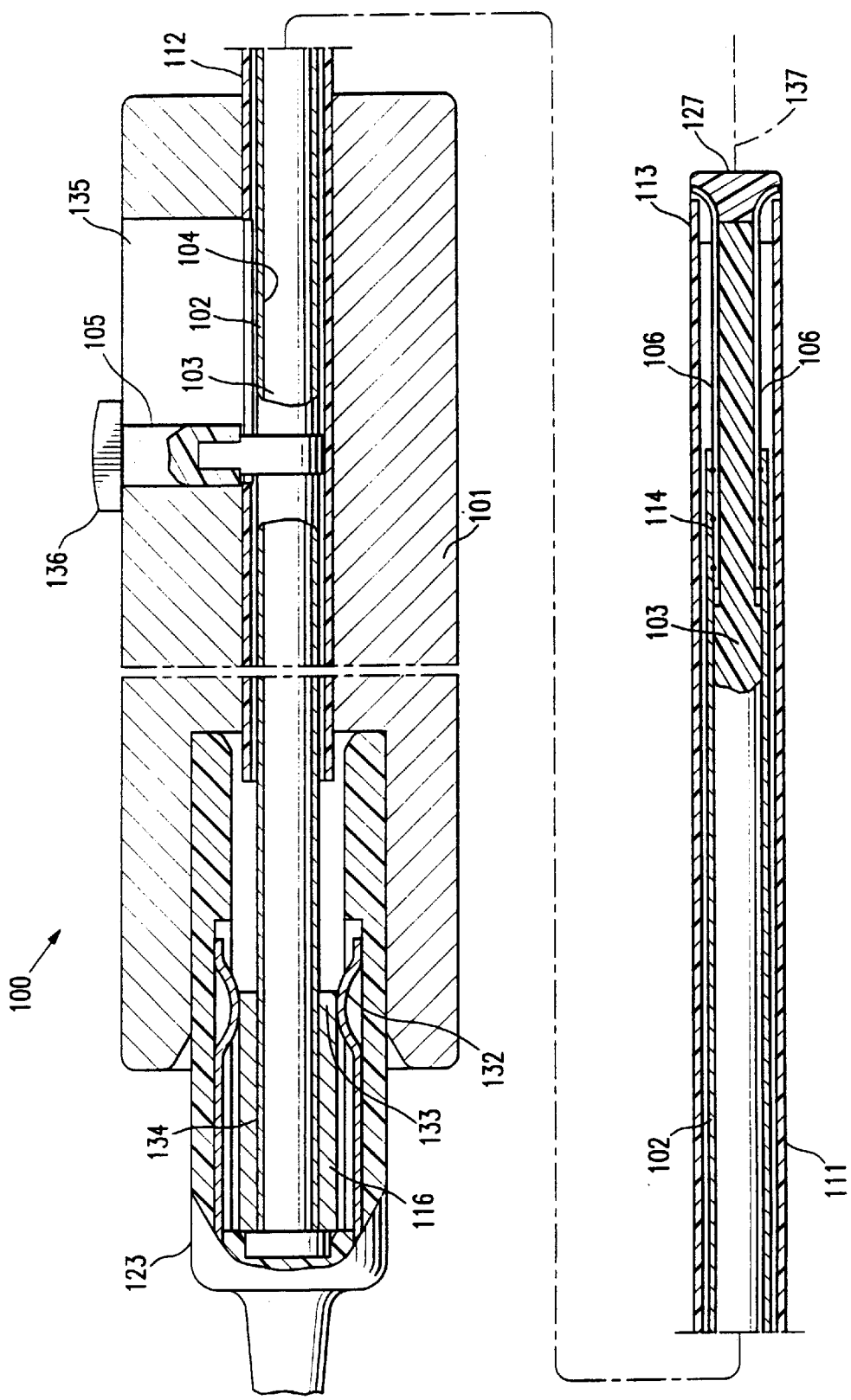
FIG. 10 is an elevational view in partial longitudinal section of an anchor device having features of the invention, wherein the extension wires at the distal end of the anchor device are in a retracted position.

FIG. 10 shows the anchor device 100 where the extension wires 106 at the distal end 127 of the anchor device 100 are in a retracted position. A spring loaded electrical contact 132 is disposed within the coupler 123 disposed on the distal end 133 of first conductor 116. The electrical contact 132 is slidingly and electrically coupled to a distal end which is secured to and in electrical communication with a proximal end 134 of the inner conductor 102. The first conductor 116 is able to slide within the spring loaded contact 132 maintaining an electrical path between conductor 116 and inner conductor 102 while allowing axial translation of the inner conductor 102 relative to the coupler 123 and housing 101.

Figure 11:
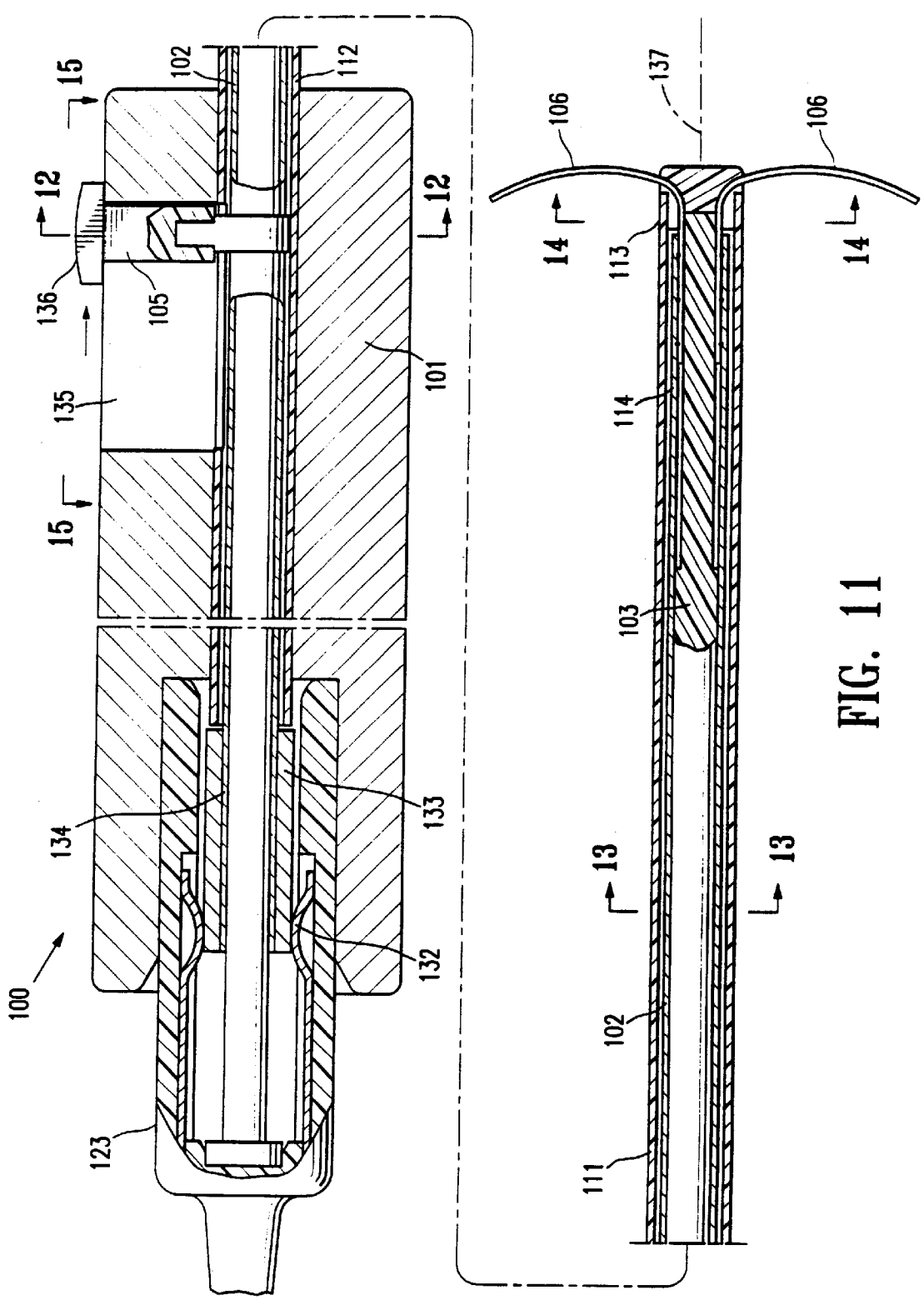
FIG. 11 is an elevational view in partial section of the anchor device of FIG. 10 with the extension wires in an expanded position extending radially outward from a longitudinal axis of the anchor device.
Figure 13:
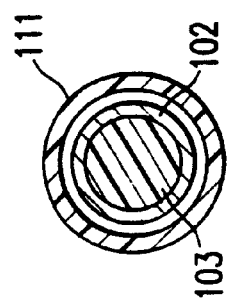
FIG. 13 is a transverse cross sectional view of the elongate shaft of the anchor device of FIG. 11 taken along lines 13—13 in FIG. 11.
Figure 12:
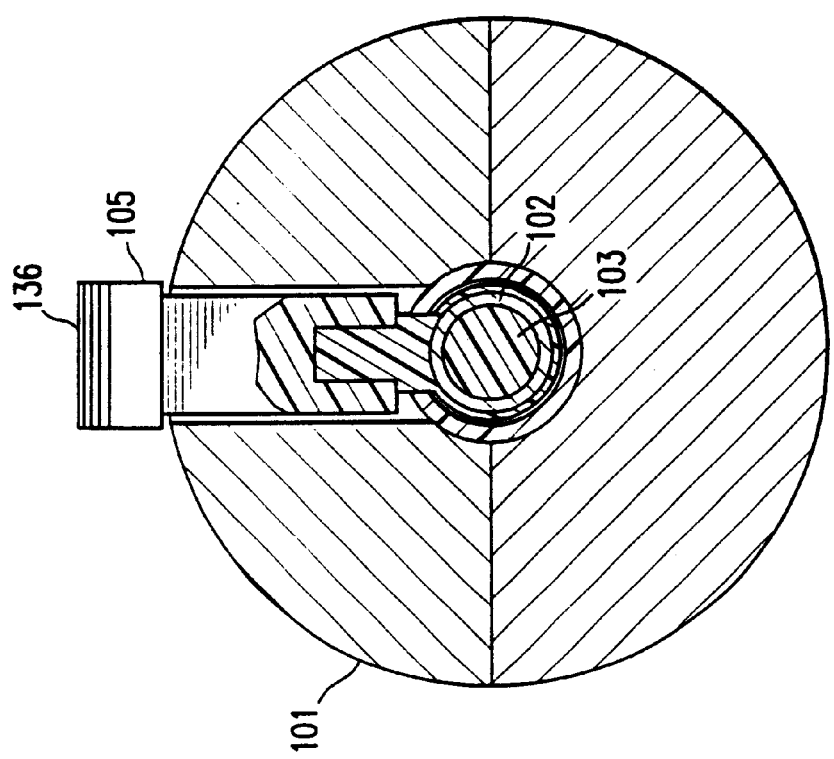
FIG. 12 is a transverse cross sectional view of a handle assembly of the anchor device of FIG. 11 taken along lines 12—12 of FIG. 11.

Actuator switch 105 is mechanically coupled to inner conductor 102 and slidingly engaged in a slot 135 in the housing 101 with an abutment 136 extending radially from the slot 135 in the housing 101 to facilitate axial movement by the operator of the anchor device 100. In FIG. 10 the actuator switch 105 and abutment 136 are in the most proximal position within the slot 135 which corresponds to the radially retracted position of the extension wires 106. FIG. 11 shows the extension wires 106 in a radially expanded position extending radially outward from a longitudinal axis 137 of the anchor device 100 with the actuator switch 105 in its corresponding most distal forward position.

FIG. 15 shows a top view of the actuator switch 105 of the anchor device 100 in a fully forward distal position corresponding to full extension of the extension wires 106 in an outward radial direction as shown in FIG. 10. Also in FIG. 15 the axial markings 115 can be more clearly seen with numerical designations which may correspond to the diameter or radius of the extension wires 106 at the distal end 127 of the anchor device 100. In FIG. 16 the anchor device 100 is being inserted into an outer hollow shaft 124 of a cannula 125 the distal end 141 of which is disposed adjacent a sentinel lymph node 126. The inner conductor 102 of the anchor device 100 is electrically coupled to a conductor 116 which is in turn electrically coupled to the RF generator 107. A ground pad 122 is in electrical contact with the patient 121 and electrically coupled to the RF generator 107 with a second conductor 117.

Figure 19:
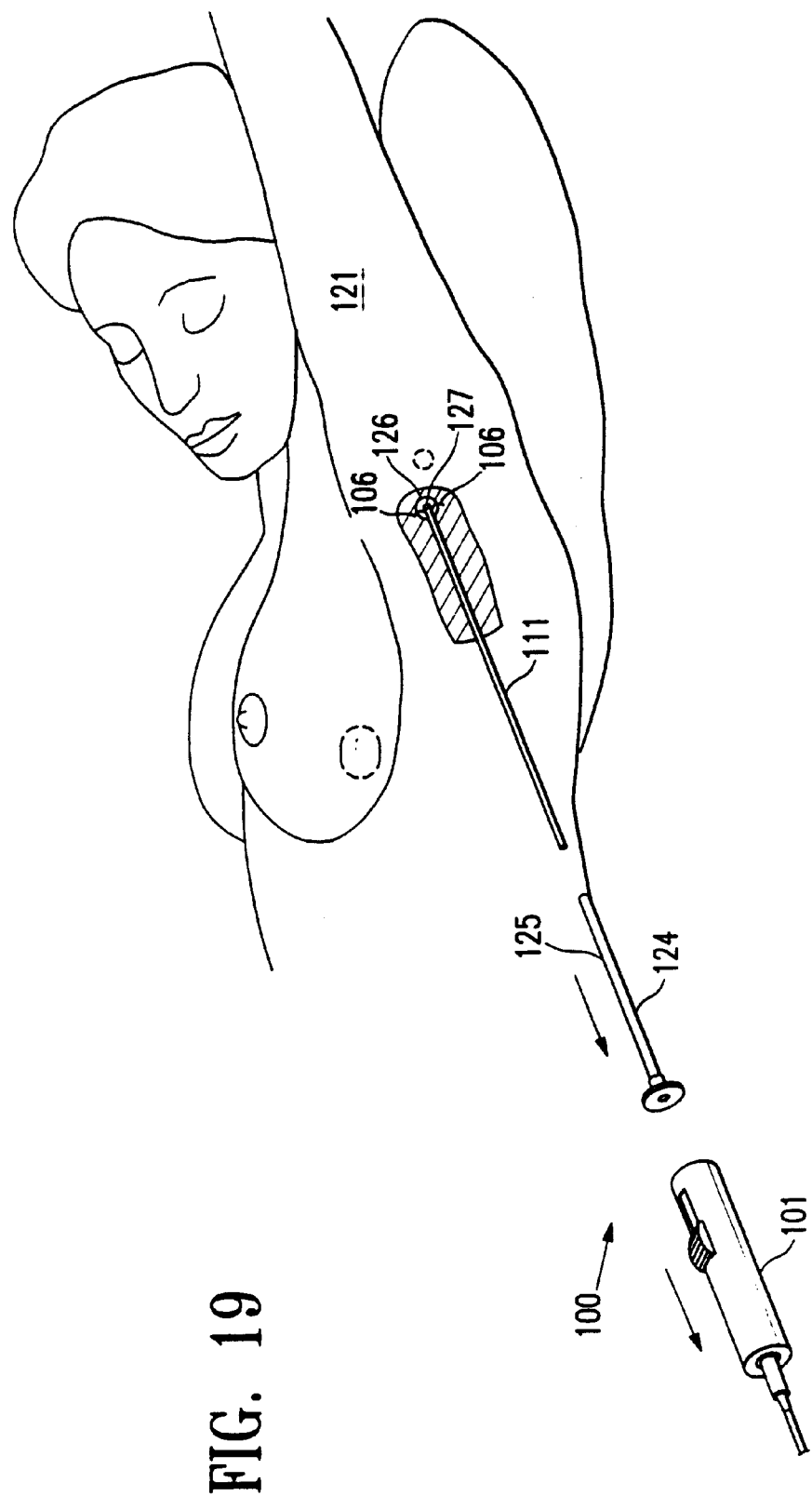
FIG. 19 is a schematic view of an outer hollow shaft of a cannula and a handle assembly of an anchor device being removed from the patient proximally with the distal shaft of the anchor device remaining within the patient with the distal end of the anchor device secured to the sentinel lymph node with the extension wires.

FIG. 17 shows the elongate shaft 111 of the anchor device 100 disposed within an inner lumen 142 of the hollow outer shaft 124 of the cannula 125. The distal end 127 of the anchor device 100 disposed within a sentinel lymph node 126 in the tissue of the patient 121 with the extension wires 106 in a retracted position. In FIG. 18, the extension wires 106 of the anchor device 100 have been extended into the sentinel lymph node 126 and mechanically secured thereto. In FIG. 19, the outer hollow shaft 124 of the cannula 125 and housing 101 of the anchor device 100 are being removed proximally from the patient 121. The elongate shaft 111 of the anchor device 100 remains within the patient 121 with the distal end 127 of the anchor device 100 secured to the sentinel lymph node 126 with the extension wires 106 in an extended position. Thereafter, the patient 121 may be taken to surgery to have the lesion excised or otherwise treated with the elongate shaft 111 of the anchor device 100 serving as a positive location means during the procedure.

In use during a typical procedure, radioactive material 15 is injected into a patient's body 10 near a primary lesion site 15 or other site of interest within the patient 10. The approximate position of a sentinel lymph node 17 within the patient's body 10 is determined by detecting radiation from the radioactive material 15 accumulated within the sentinel lymph node 17 with a radiation detector 21 or 22 external to the patient's body 10. The sentinel lymph node 17 can then be accessed with a cannula 37 having an RF electrode 41 disposed on a distal end 42 of the cannula 37 by activating the RF electrode to ablate tissue while passing the cannula into the patient's body 10 until the distal end 42 of the cannula 37 is disposed adjacent the sentinel lymph node 17.

Once the distal end 42 of the cannula 37 is positioned adjacent the sentinel lymph node 17, the proximity of the distal end 42 of the cannula 37 to the sentinel lymph node 17 can be optimized by inserting a radiation energy detector probe 74 into an inner lumen of a hollow outer shaft 55 of the cannula 37 and manipulating a distal end 76 of the radiation energy detector probe 74 so as to positively identify the position of the targeted sentinel node 17 by maximizing radiation energy received by the radiation energy probe from the targeted sentinel node.

An anchor device 100 can then be inserted through the cannula 37 and into the sentinel lymph node 17. The distal end 127 of the anchor device 100 can then be secured to the sentinel lymph node 17. Once the distal end 127 of the anchor device 100 is secured to the lymph node 17, the patient 10 can be transferred to a surgical suite and the lymph node 17 surgically removed with the anchor device 100 or a portion thereof attached thereto.

Figure 20:
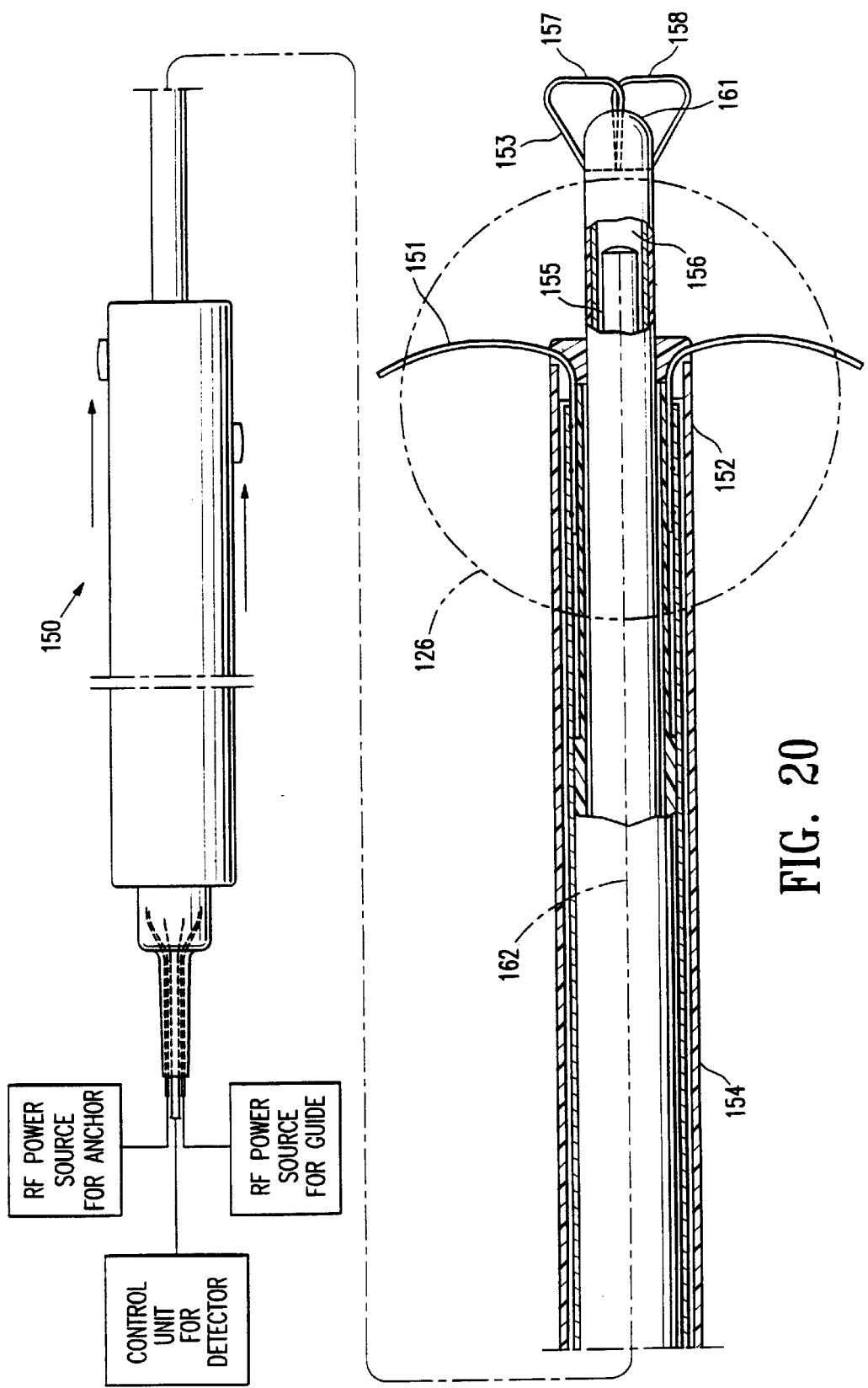
FIG. 20 is an elevational view in partial section of an anchor device having features of the invention including extension wires which are radially extendable from the distal end of the anchor device, an expandable RF electrode on the distal end of the anchor device and a radiation detector probe disposed within an inner lumen of the anchor device and which is optionally axially moveable within the inner lumen of the anchor device.

Referring to FIG. 20, an alternative embodiment of an anchor device 150 is shown having features of the invention. The anchor device 150 has extension wires 151 which are radially extendable from the distal end 152 of the anchor device 150, an expandable RF electrode 153 on the distal end 152 of an elongate shaft 154 of the anchor device 150 and a radiation detector probe 155 which is disposed within an inner lumen 156 of the anchor device 150 and which is optionally axially moveable within the inner lumen 156 of the anchor device 150.

The RF electrode 153 is configured to ablate and penetrate tissue in a manner similar to the RF electrode 41 on the distal end 42 of the cannula 41 37 discussed above. The RF electrode 153 on the distal end 152 of the elongate shaft 154 is an arcuate wire having two separate electrode elements, a first electrode element 157 and a second electrode element 158, spaced distally from a distal extremity 161 of the distal end 152 of the elongate shaft 154. The RF electrode 153 of the embodiment shown lies in substantially the same plane as a longitudinal axis 162 of the elongate shaft 154 of the anchor device 150.

In use during a typical procedure for this embodiment, radioactive material is injected into a patient's body near a primary lesion site or other site of interest within the patient. The approximate position of a sentinel lymph node within the patient's body is determined by detecting radiation from the radioactive material accumulated within the sentinel lymph node with a radiation detector external to the patient's body. The sentinel lymph node (shown in phantom in FIG. 20) can then be accessed with the anchor device 150 having the RF electrode 153 disposed on a distal end 152 of the anchor device 150 by activating the RF electrode 153 to ablate tissue while passing the distal end 152 of the anchor device into the patient's body until the distal end 152 of the anchor device is disposed adjacent the sentinel lymph node.

Once the distal end 152 of the anchor device 150 is positioned adjacent the sentinel lymph node, the proximity of the distal end 152 of the anchor device to the sentinel lymph node can be optimized by manipulating the distal end of the anchor device so as to maximize signal output by the radiation energy detector 155 within the anchor device 150. The distal end 152 of the anchor device 150 can be secured to the sentinel lymph node by the extension of extension wires 151 into the node. Once the distal end 152 of the anchor device 150 is secured to the lymph node, the patient can be transferred to a surgical suite and the lymph node surgically removed with the anchor device attached thereto.

While particular forms of the invention have been illustrated and described, it should be apparent that various modifications can be made without departing from the spirit and scope of the invention. Accordingly, it is not intended that the invention be limited, except as by the appended claims.

What is claimed is:

1. A system for accessing and anchoring a desired portion of tissue within a patient, comprising:
    a) a tissue accessing device having an elongated cannula with a proximal end, a port in the proximal end, a distal end and a port in the distal end, and an inner lumen in fluid communication with the ports in the proximal and distal ends; and
    b) an anchoring device configured to be slidably disposed within the inner lumen of the cannula, having
        i. an elongated shaft having a proximal end and a distal end,
        ii. at least one opening on the distal end configured to guide an extension wire in a radial direction away from the distal end,
        iii. at least one extension wire within the elongated shaft which has a free end, which has a withdrawn configuration within the elongated shaft, which has a deployed configuration when extended through the opening in the distal end so the free end of the extension wire extends for a distance radially away from the distal end of the shaft, and
        iv. a deployment actuator which is configured to deploy the extension wire from the withdrawn configuration to the deployed configuration.

2. The system of claim 1 wherein the tissue penetrating member is an RF electrode.

3. The system of claim 2 wherein the RF electrode comprises an arcuate wire spaced distally from the distal extremity of the distal end of the elongate shaft.

4. The system of claim 2 wherein the RF electrode lies in substantially the same plane as the longitudinal axis of the elongate shaft of the anchoring device.

5. The system of claim 1 wherein the anchoring device further comprises markings spaced at predetermined intervals to indicate said extension distance of the at least one extension wire.

6. The system of claim 1 wherein the anchoring device further comprises a first electrical lead electrically coupled to the one extension wire and a second electrical lead which is configured to be electrically coupled to the patient whereby RE energy can be applied to the one extension wire during deployment and extension thereof.

7. The system of claim 6 wherein the first electrical lead of the anchoring device is coupled to the extension wire at the proximal end of the shaft with a detachable connector.

8. The system of claim 1 wherein the deployment actuator of the anchoring device is configured to both extend at least one extension wire and activate RF energy to the at least one extension wire.

9. The system of claim 1 wherein the anchoring device includes a housing, an inner conductor, a main shaft disposed within an inner lumen of the inner conductor, an actuator coupled to the inner conductor for extending the extension wires and an RF energy source switchably coupled to the inner conductor.

10. The system of claim 1 wherein the accessing probe has an inner lumen and an elongated radiation detection probe is slidably disposed within the inner lumen of the accessing probe.

* * * * *

UNITED STATES PATENT AND TRADEMARK OFFICE
CERTIFICATE OF CORRECTION

PATENT NO. : 6,716,179 B2
DATED : April 6, 2004
INVENTOR(S) : Burbank et al.

It is certified that error appears in the above-identified patent and that said Letters Patent is hereby corrected as shown below:

Column 13,
Line 17, after "distal ends;" delete "and".
Line 20, after "proximal end" delete "and".
Line 21, change "end," to -- end and an inner lumen extend on therein, --.
Line 25, after "extension wire" insert -- which is disposed at least in part --.
Line 26, after "shaft" insert -- , --.
Line 27, after "shaft" insert -- and --.
Line 34, change "configuration." to -- configuration; and --.
Line 35, insert -- c. an accessing probe which is slidably disposed within the linner lumen of the anchoring device and which has a distal end with a tissue penetrating member. --.

Column 14,
Line 13, after "to" delete "the" and insert -- at least --.
Line 15, delete "whereby RE energy can be applied to the" and insert -- to apply RF energy to at least --.
Line 18, after "coupled to" delete "the" and insert -- at least one --.
Line 26, after "inner conductor," delete "an" and insert -- wherein the --.
Line 27, after "actuator" insert -- is -- and after "for extending" delete "the" and insert -- at least one --.
Line 28, change "extension wires and an RF energy source" to -- extension wire and wherein an RF energy source is --.

Signed and Sealed this

Twenty-sixth Day of April, 2005

JON W. DUDAS
*Director of the United States Patent and Trademark Office*